United States Patent
Oh et al.

(10) Patent No.: US 11,051,715 B2
(45) Date of Patent: Jul. 6, 2021

(54) IMAGE PROCESSING APPARATUS, IMAGE PROCESSING METHOD, AND RECORDING MEDIUM RECORDING SAME

(71) Applicant: Samsung Electronics Co., Ltd., Suwon-si (KR)

(72) Inventors: Ji-hun Oh, Hwaseong-si (KR); Woo-hyun Nam, Seoul (KR); Yong-sup Park, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 265 days.

(21) Appl. No.: 16/061,201

(22) PCT Filed: Dec. 23, 2016

(86) PCT No.: PCT/KR2016/015141
§ 371 (c)(1),
(2) Date: Jun. 11, 2018

(87) PCT Pub. No.: WO2017/142183
PCT Pub. Date: Aug. 24, 2017

(65) Prior Publication Data
US 2018/0368731 A1    Dec. 27, 2018

(30) Foreign Application Priority Data
Feb. 15, 2016   (KR) .................. 10-2016-0017484

(51) Int. Cl.
*A61B 5/091*     (2006.01)
*A61B 6/03*      (2006.01)
(Continued)

(52) U.S. Cl.
CPC ............ *A61B 5/091* (2013.01); *A61B 5/0035* (2013.01); *A61B 5/0816* (2013.01); *A61B 5/113* (2013.01);
(Continued)

(58) Field of Classification Search
CPC ..... A61B 5/0035; A61B 5/0816; A61B 5/091; A61B 5/113; A61B 6/00; A61B 6/03;
(Continued)

(56) References Cited

U.S. PATENT DOCUMENTS

| 5,719,630 A | * | 2/1998 | Senda | ................... | H04N 19/105 |
| | | | | | 348/699 |
| 6,348,954 B1 | * | 2/2002 | Takishima | .............. | G06T 9/008 |
| | | | | | 348/699 |

(Continued)

FOREIGN PATENT DOCUMENTS

| JP | 2005-028121 A | | 2/2005 |
| JP | 2013074468 A | * | 4/2013 |

(Continued)

OTHER PUBLICATIONS

David Rey et al., "Automatic detection and segmentation of evolving processes in 3D medical images: Application to multiple sclerosis", Jun. 2002, pp. 163-179 (Year: 2002).*

*Primary Examiner* — Mekonen T Bekele
(74) *Attorney, Agent, or Firm* — Jefferson IP Law, LLP

(57) ABSTRACT

The present invention relates to an image processing apparatus, an image processing method, and a recording medium for recording the same, the image processing apparatus including a storage configured to comprise a standard database (DB) established based on information about a predetermined anatomical entity; and at least one processor configured to obtain a local motion vector by registration between a first medical image and a second medical image taken by scanning an object including the anatomical entity, use a predictive local motion vector generated from the standard DB to normalize the local motion vector according to a plurality of regions in the anatomical entity, and make information about conditions of the anatomical entity based on the normalized local motion vector be provided accord- (Continued)

ing to the plurality of regions. By the normalization according to the regions, it is possible to provide distinguishable information about difference between the local motion vector of a pulmonary disease patient to be subjected to a diagnosis and a predictive local motion vector of a normal person generated from the standard DB through the statistical modeling using bio-information of a patient.

15 Claims, 27 Drawing Sheets

(51) Int. Cl.
| | |
|---|---|
| *A61B 5/113* | (2006.01) |
| *G16H 50/20* | (2018.01) |
| *A61B 6/00* | (2006.01) |
| *G16H 30/40* | (2018.01) |
| *G16H 40/63* | (2018.01) |
| *G06T 7/00* | (2017.01) |
| *A61B 5/00* | (2006.01) |
| *G16H 30/20* | (2018.01) |
| *A61B 5/08* | (2006.01) |
| *G06T 7/20* | (2017.01) |

(52) U.S. Cl.
CPC ............... *A61B 6/00* (2013.01); *A61B 6/03* (2013.01); *A61B 6/5211* (2013.01); *G06T 7/0016* (2013.01); *G06T 7/20* (2013.01); *G16H 30/20* (2018.01); *G16H 30/40* (2018.01); *G16H 40/63* (2018.01); *G16H 50/20* (2018.01); *A61B 6/032* (2013.01); *G06T 2207/10081* (2013.01); *G06T 2207/10088* (2013.01); *G06T 2207/20021* (2013.01); *G06T 2207/30061* (2013.01)

(58) Field of Classification Search
CPC ..... A61B 6/5211; A61B 6/032; G06T 7/0016; G06T 7/20; G06T 2207/10081; G06T 2207/10088; G06T 2207/20021; G06T 2207/30061; G16H 30/20; G16H 30/40; G16H 40/63; G16H 50/20
See application file for complete search history.

(56) References Cited

U.S. PATENT DOCUMENTS

| | | | | |
|---|---|---|---|---|
| 9,609,330 | B2* | 3/2017 | Puri | H04N 19/122 |
| 2004/0057523 | A1* | 3/2004 | Koto | H04N 19/132 |
| | | | | 375/240.26 |
| 2010/0111436 | A1* | 5/2010 | Jung | G06K 9/40 |
| | | | | 382/263 |
| 2011/0081054 | A1 | 4/2011 | Bell et al. | |
| 2011/0142133 | A1* | 6/2011 | Takahashi | G06N 3/10 |
| | | | | 375/240.16 |
| 2011/0170658 | A1* | 7/2011 | Arakita | G06T 11/008 |
| | | | | 378/8 |
| 2011/0293010 | A1* | 12/2011 | Jeong | H04N 19/176 |
| | | | | 375/240.16 |
| 2012/0189167 | A1* | 7/2012 | Kurata | G06T 7/238 |
| | | | | 382/107 |
| 2012/0288173 | A1* | 11/2012 | Rai | G06T 17/00 |
| | | | | 382/131 |
| 2012/0320985 | A1* | 12/2012 | Kitahara | H04N 19/521 |
| | | | | 375/240.16 |
| 2013/0004044 | A1 | 1/2013 | Ross et al. | |
| 2013/0022124 | A1* | 1/2013 | Sekiguchi | H04N 19/46 |
| | | | | 375/240.16 |
| 2013/0155228 | A1* | 6/2013 | Fam | H04N 19/543 |
| | | | | 348/143 |
| 2014/0072193 | A1* | 3/2014 | Motomura | G06T 7/0012 |
| | | | | 382/128 |
| 2014/0362922 | A1* | 12/2014 | Puri | H04N 19/167 |
| | | | | 375/240.16 |
| 2015/0005659 | A1 | 1/2015 | Masumoto | |
| 2015/0312588 | A1* | 10/2015 | Yamamoto | H04N 19/44 |
| | | | | 375/240.15 |
| 2016/0022240 | A1 | 1/2016 | Yamagata et al. | |
| 2016/0148375 | A1* | 5/2016 | Oh | G16H 30/20 |
| | | | | 382/131 |
| 2017/0118484 | A1* | 4/2017 | Maeda | H04N 19/176 |
| 2017/0221234 | A1* | 8/2017 | Chen | G06T 5/002 |

FOREIGN PATENT DOCUMENTS

| | | |
|---|---|---|
| KR | 10-2013-0030663 A | 3/2013 |
| KR | 10-2015-0118484 A | 10/2015 |

* cited by examiner

FIG. 7
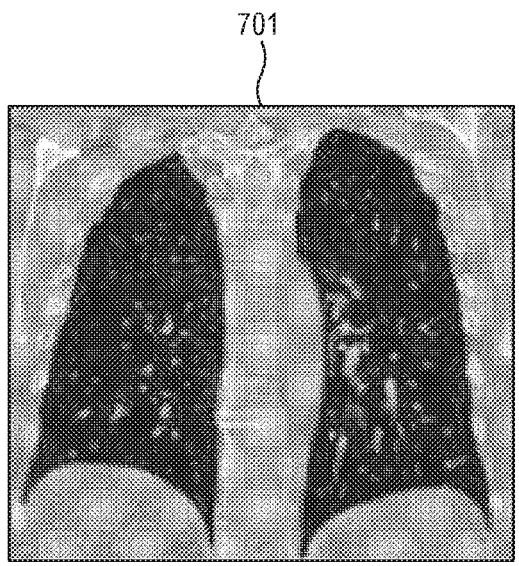
FIRST MEDICAL IMAGE
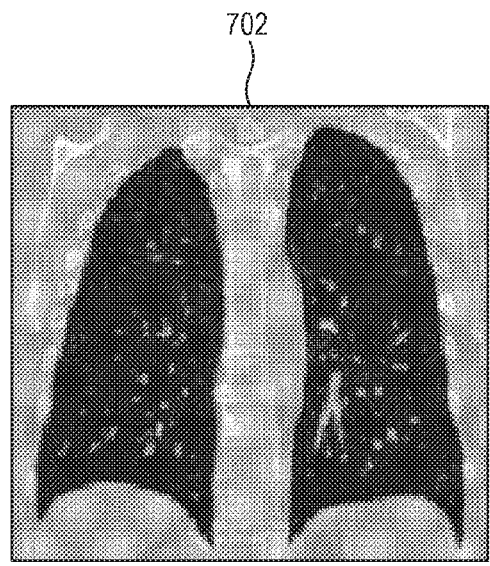
SECOND MEDICAL IMAGE

LOCAL MOTION VECTOR

PREDICTIVE LOCAL MOTION VECTOR

MOTION ANALYSIS

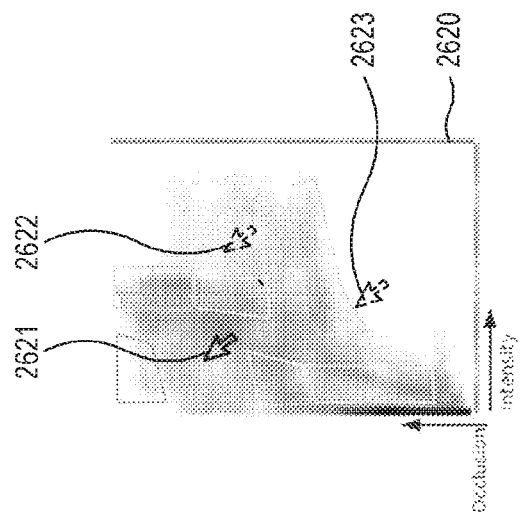
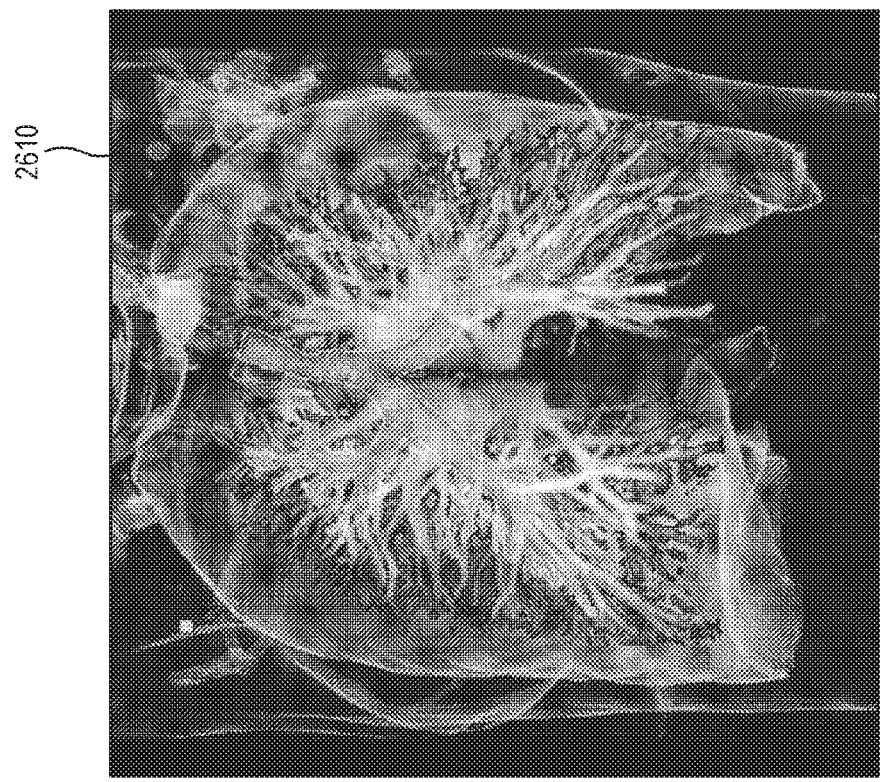
FIG. 26

IMAGE PROCESSING APPARATUS, IMAGE PROCESSING METHOD, AND RECORDING MEDIUM RECORDING SAME

TECHNICAL FIELD

The present invention relates to an image processing apparatus, an image processing method, and a recording medium for recording the same, in which a medical image and statistical standard information are used to provide information for diagnosing condition of a predetermined entity.

BACKGROUND ART

A medical image provides an internal structure of an object, and shows structural details, internal organs, fluid flow, etc. inside a scanned and processed body to a user.

As the medical image, there are a magnetic resonance image for magnetic resonance imaging (MRI), a computed tomography (CT) image, an X-ray image, an ultrasound image, etc. The medical image represents an object in various forms according to the kinds of scanning device and scanning methods.

A doctor or the like user uses such a medical image to check health conditions of a patient and diagnose a disease. For example, a pulmonary CT image of a lung may be used in diagnosing a lung disease.

The pulmonary CT image is used for diagnosing various pulmonary diseases, and there is a need of providing an image involving information required for a diagnostic purpose to make an accurate diagnosis.

For example, in a case of a chronic obstructive pulmonary disease (COPD) that is the third cause of death in the world, there may be a need of providing information for precisely diagnosing regions of a lung. Further, values of measuring airway wall and lumen sizes may be provided in a case of an airway-related disease, and information about pulmonary tissue analysis may be provided in a case of pulmonary emphysema. Further, in a case of a blood-vessel related disease, segmentation and size-analysis of blood vessels may be needed from the medical image.

Therefore, there is a demand for image processing capable of providing more accurate diagnosis results of a pulmonary function through the medical image, more specifically, the pulmonary CT image.

DISCLOSURE

Technical Solution

According to one embodiment of the present invention the image processing apparatus includes a storage configured to include a standard database (DB) established based on information about a predetermined anatomical entity; and at least one processor configured to obtain a local motion vector by registration between a first medical image and a second medical image taken by scanning an object including the anatomical entity, use a predictive local motion vector generated from the standard DB to normalize the local motion vector according to a plurality of regions in the anatomical entity, and make information about conditions of the anatomical entity based on the normalized local motion vector be provided according to the plurality of regions. Thus, the normalized information is provided according to the regions, thereby diagnosing a disease of a certain entity according to the regions.

A display may be further provided to display the information about the conditions of the anatomical entity distinguishable according to the plurality of regions. Thus, a user can more accurately and segmentally make a diagnosis based on the information displayed according to the regions.

The processor may extract a region corresponding to the anatomical entity from the first medical image and the second medical image, and obtain the local motion vector corresponding to a displacement vector derived by the registration between the first medical image and the second medical image from which the region of the anatomical entity is extracted. Thus, the present invention is utilized in diagnosing a certain entity.

The anatomical entity may include a lung, and the first medical image may correspond to an inspiratory image and the second medical image may correspond to an expiratory image. Thus, the present invention is applicable to the pulmonary disease.

The standard DB may be established by vectorizing a plurality of medical images collected with regard to the anatomical entity, and applying statistical modeling to vectorized data. Thus, it is possible to provide the diagnosis information corresponding to difference between information about a pulmonary disease patient and statistical standard information.

The processor may receive bio-information about a patient to be subjected to a diagnosis as a variable, and compute the predictive local vector by applying the received variable to a function corresponding to the standard DB. Thus, it is possible to obtain standard information by a simple mathematical operation.

The bio-information about a patient may include at least one among physical information, biological information and habitual information. Thus, a diagnosis can be made by considering effects of the physical, biological and habitual information or the like on the disease.

The established standard DB may further include local motion vector information corresponding to the plurality of medical images, and the processor may search the local motion vector corresponding to bio-information about a patient to be subjected to a diagnosis from the standard DB, and determine the predictive local motion vector based on results of the search. Thus, it is possible to utilize the standard data adapted to a patient.

The processor may select two or more local motion vectors having similar bio-information to the patient, and compute the predictive local motion vector by applying interpolation to the two or more selected local motion vectors. Thus, a diagnosis can be made using the standard data similar to the conditions of a patient.

The processor may register a predictive local motion vector generated from the standard DB to a third medical image generated by registration between the first medical image and the second medical image, and use the predictive local motion vector warped to the third medical image by the registration to normalize the local motion vector according to the plurality of regions. Thus, a more accurate diagnosis can be made using the information approximately equal to the conditions of a patient.

The processor may perform a motion analysis based on a normalized local motion vector according to the plurality of regions, computes at least one factor indicating kinematic function ability normalized according to results of the analysis, and provide diagnosis information of the anatomical entity corresponding to the at least one calculated factor according to the plurality of regions. Thus, an accurate diagnosis function is provided according to the motion analysis.

The anatomical entity may include a lung, and the processor may provide diagnosis information about the lung through at least one factor, and provide the standard information about the patient to be subjected to the diagnosis together with the diagnosis information. Thus, a user can compare and use the standard information and information about a patient for a diagnosis.

Meanwhile, according to one embodiment of the present invention, an image processing method includes a step of obtaining a local motion vector by registration between a first medical image and a second medical image taken by scanning an object including a predetermined anatomical entity; a step of using a predictive local motion vector generated from a standard DB including information about the anatomical entity to normalize the local motion vector according to a plurality of regions in the anatomical entity; and a step of making information about conditions of the anatomical entity based on the normalized local motion vector be provided according to the plurality of regions. Thus, the normalized information is provided according to the regions, thereby diagnosing a disease of a certain entity according to the regions.

A step is further provided to display the information about the conditions of the anatomical entity distinguishable according to the plurality of regions. Thus, a user can more accurately and segmentally make a diagnosis based on the information displayed according to the regions.

The step of obtaining the local motion vector may include: a step of extracting a region corresponding to the anatomical entity from the first medical image and the second medical image; and a step of obtaining the local motion vector corresponding to a displacement vector derived by the registration between the first medical image and the second medical image from which the region of the anatomical entity is extracted. Thus, the present invention is utilized in diagnosing a certain entity.

The anatomical entity may include a lung, and the first medical image may correspond to an inspiratory image and the second medical image may correspond to an expiratory image. Thus, the present invention is applicable to the pulmonary disease.

There may be further provided a step of vectorizing a plurality of medical images collected with regard to the anatomical entity; and a step of establishing the standard DB by applying statistical modeling to the vectorized data. Thus, it is possible to provide the diagnosis information corresponding to difference between information about a pulmonary disease patient and statistical standard information.

There may be further provided a step of receiving bio-information about a patient to be subjected to a diagnosis as a variable; and a step of computing the predictive local vector by applying the received variable to a function corresponding to the standard DB, wherein the step of the normalization according to the plurality of regions uses the computed predictive local vector. Thus, it is possible to obtain standard information by a simple mathematical operation.

The bio-information about a patient may include at least one among physical information, biological information and habitual information. Thus, a diagnosis can be made by considering effects of the physical, biological and habitual information or the like on the disease.

The established standard DB may further include local motion vector information corresponding to the plurality of medical images, and the method may further include a step of searching the local motion vector corresponding to bio-information about a patient to be subjected to a diagnosis from the standard DB; and a step of determining the predictive local motion vector based on results of the search, and the step of the normalization according to the plurality of regions may use the determined predictive local motion vector. Thus, it is possible to utilize the standard data adapted to a patient.

There may be further provided a step of selecting two or more local motion vectors having similar bio-information to the patient, and the step of determining the predictive local motion vector may include a step of computing the predictive local motion vector by applying interpolation to the two or more selected local motion vectors. Thus, a diagnosis can be made using the standard data similar to the conditions of a patient.

There may be further provided a step of registering a predictive local motion vector generated from the standard DB to a third medical image generated by registration between the first medical image and the second medical image, and the step of the normalization according to the plurality of regions may use the predictive local motion vector warped to the third medical image by the registration to normalize the local motion vector according to the plurality of regions. Thus, a more accurate diagnosis can be made using the information approximately equal to the conditions of a patient.

There may be further provided a step of performing a motion analysis based on a normalized local motion vector according to the plurality of regions, a step of computing at least one factor indicating kinematic function ability normalized according to results of the analysis, and a step of providing diagnosis information of the anatomical entity corresponding to the at least one calculated factor according to the plurality of regions. Thus, an accurate diagnosis function is provided according to the motion analysis.

The anatomical entity may include a lung, and the step of providing according to the plurality of regions may provide diagnosis information about the lung through at least one factor, and provide the standard information about the patient to be subjected to the diagnosis together with the diagnosis information.

Meanwhile, according to one embodiment of the present invention, a recording medium recorded with a program for performing an image processing method as a computer readable program, the image processing method including a step of obtaining a local motion vector by registration between a first medical image and a second medical image taken by scanning an object including a predetermined anatomical entity; a step of using a predictive local motion vector generated from a standard DB including information about the anatomical entity to normalize the local motion vector according to a plurality of regions in the anatomical entity; and a step of making information about conditions of the anatomical entity based on the normalized local motion vector be provided according to the plurality of regions. Thus, the normalized information is provided according to the regions, thereby diagnosing a disease of a certain entity according to the regions.

A step is further provided to display the information about the conditions of the anatomical entity distinguishable according to the plurality of regions. Thus, a user can more accurately and segmentally make a diagnosis based on the information displayed according to the regions.

The step of obtaining the local motion vector may include: a step of extracting a region corresponding to the anatomical entity from the first medical image and the second medical image; and a step of obtaining the local motion vector corresponding to a displacement vector derived by the registration between the first medical image and the second medical image from which the region of the anatomical entity is extracted. Thus, the present invention is utilized in diagnosing a certain entity.

The anatomical entity may include a lung, and the first medical image may correspond to an inspiratory image and the second medical image may correspond to an expiratory image. Thus, the present invention is applicable to the pulmonary disease.

There may be further provided a step of vectorizing a plurality of medical images collected with regard to the anatomical entity; and a step of establishing the standard DB by applying statistical modeling to the vectorized data. Thus, it is possible to provide the diagnosis information corresponding to difference between information about a pulmonary disease patient and statistical standard information.

There may be further provided a step of receiving bio-information about a patient to be subjected to a diagnosis as a variable; and a step of computing the predictive local vector by applying the received variable to a function corresponding to the standard DB, wherein the step of the normalization according to the plurality of regions uses the computed predictive local vector. Thus, it is possible to obtain standard information by a simple mathematical operation.

The bio-information about a patient may include at least one among physical information, biological information and habitual information. Thus, a diagnosis can be made by considering effects of the physical, biological and habitual information or the like on the disease.

The established standard DB may further include local motion vector information corresponding to the plurality of medical images, and the method may further include a step of searching the local motion vector corresponding to bio-information about a patient to be subjected to a diagnosis from the standard DB; and a step of determining the predictive local motion vector based on results of the search, and the step of the normalization according to the plurality of regions may use the determined predictive local motion vector. Thus, it is possible to utilize the standard data adapted to a patient.

There may be further provided a step of selecting two or more local motion vectors having similar bio-information to the patient, and the step of determining the predictive local motion vector may include a step of computing the predictive local motion vector by applying interpolation to the two or more selected local motion vectors. Thus, a diagnosis can be made using the standard data similar to the conditions of a patient.

There may be further provided a step of registering a predictive local motion vector generated from the standard DB to a third medical image generated by registration between the first medical image and the second medical image, and the step of the normalization according to the plurality of regions may use the predictive local motion vector warped to the third medical image by the registration to normalize the local motion vector according to the plurality of regions. Thus, a more accurate diagnosis can be made using the information approximately equal to the conditions of a patient.

There may be further provided a step of performing a motion analysis based on a normalized local motion vector according to the plurality of regions, a step of computing at least one factor indicating kinematic function ability normalized according to results of the analysis, and a step of providing diagnosis information of the anatomical entity corresponding to the at least one calculated factor according to the plurality of regions. Thus, an accurate diagnosis function is provided according to the motion analysis.

The anatomical entity may include a lung, and the step of providing according to the plurality of regions may provide diagnosis information about the lung through at least one factor, and provide the standard information about the patient to be subjected to the diagnosis together with the diagnosis information.

DESCRIPTION OF DRAWINGS

FIGS. 6 to 14 are views for showing a process for providing information about conditions of a predetermined anatomical entity in an image processing apparatus according to a first embodiment of the present invention, FIGS. 26 and 27 are views of showing examples that the image processing apparatus according to the third embodiment of the present invention displays a reconfigured integrated CT readout image.

BEST MODE

Figure 1:
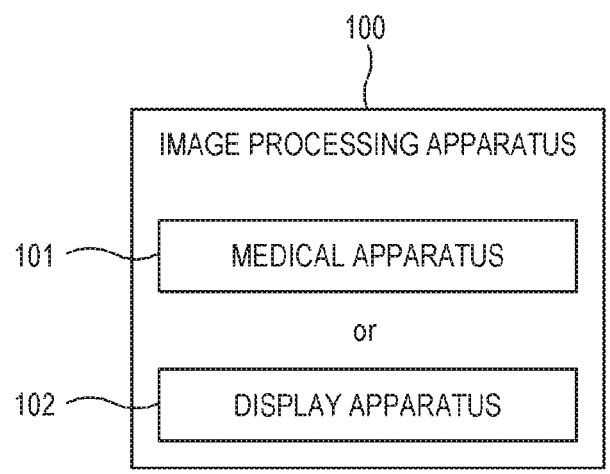
FIG. 1 is a view for explaining an image processing apparatus according to one embodiment of the present invention.

Below, exemplary embodiments will be described with reference to accompanying drawings to such an extent as to be easily realized by a person having an ordinary knowledge in the art. The present inventive concept is not limited to the embodiments set forth herein, and may be materialized variously.

Terms to be used in the following descriptions will be selected as general terms currently used as widely as possible taking functions of elements into account, but may be varied depending on intent of those skilled in the art, precedents, the advent of new technology, etc. In particular, there may be a term voluntarily selected by the applicant. In this case, the meaning of the term will be explained in detail through the relevant detailed descriptions. Therefore, the terms set forth herein have to be read in light of its meaning and content throughout the following descriptions rather than naming.

In the following descriptions, terms such as "include" or "have" refer to presence of features, numbers, steps, operations, elements or combination thereof, and do not exclude presence or addition of one or more other features, numbers, steps, operations, elements or combination thereof.

A "portion" set forth herein refers to software or hardware such as a field-programmable gate array (FPGA) or an application-specific integrated circuit (ASIC), and performs certain roles. However, the meaning of the "portion" is not limited to software or hardware. The "portion" may be configured to be present in a storage medium for addressing or may be configured to reproduce one or more processors. For example, the "portion" includes software elements, object-oriented software elements, class elements, task elements and the like elements, and processes, functions, attributes, procedures, subroutines, segments of a program code, drivers, firmware, a microcode, a circuit, data, a database, data structures, tables, arrays and variables. The function provided in the elements and the "portions" may be carried out by combining fewer elements and "portions" or may be subdivided by additional elements and "portions".

In this specification, an "image" may indicate multi-dimensional data configured with discrete image elements (for example, pixels in a two-dimensional (2D) image and voxels in a three-dimensional (3D) image). For example, the image may include a medical image and the like of an object, obtained by X-ray, a computed tomography (CT), a magnetic resonance imaging (MRI), ultrasound and other medical imaging systems.

Further, in this specification, an "object" may include a human or an animal, or a part of the human or animal. For example, the object may include a liver, a heart, a uterus, a brain, a breast, an abdomen and the like organs, muscles or a blood vessel. Further, the "object" may include a phantom. The phantom refers to a material having a volume, which is very approximate to the density and the effective atomic number of living things, and may include a sphere phantom having similar properties to a human body.

Further, in this specification, a "user" refers to a medical expert such as a doctor, a nurse, a medical laboratory technologist, a medical image specialist, etc., a technician of repairing a medical device, or a patient, but is not limited thereto.

For clarity of the present invention in association with the drawings, portions not directly related to the elements of the present invention may be omitted, and like numerals refer to like elements throughout.

FIG. 1 is a view for describing an image processing apparatus 100 according to one embodiment of the present invention.

According to one embodiment of the present invention, the image processing apparatus 100 may be an apparatus that obtains a medical image and displays the obtained medical image on a screen. For example, as shown in FIG. 1, the image processing apparatus 100 may be a computed tomography apparatus (hereinafter, referred to as a CT apparatus) as a medical apparatus 101.

The CT apparatus 101 has advantages of providing a cross-section image of an object and showing the internal structure (e.g. organs such as a kidney, a lung, etc. or muscles such as a diaphragm) of the object without overlapping as compared with general X-ray apparatus. For example, the CT apparatus 101 may provide a relatively accurate cross-section image with regard to an object by obtaining and processing tens or hundreds of images corresponding to a thickness of 2 mm or less per second.

According to another embodiment, the image processing apparatus 100 of the present invention includes a display apparatus 102 for processing a medical image to be displayable. The display apparatus 102 may be achieved in various forms such as a desktop computer, a smart TV or the like having an image processing function, and may be achieved in the form of a mobile terminal as well as a stationary terminal. As an example of the display apparatus 102 materialized as the mobile terminal, there are a smart phone, a smart pad such as a tablet computer, a smart TV, a desktop computer, a laptop computer, a personal digital assistant (PDA), etc.

According to one embodiment, the display apparatus 102 may be installed with a predetermined application as a platform capable of processing or analyzing a medical image.

According to one embodiment, execution of an application may cause a screen to be displayed including an input region in which various buttons are positioned as a user interface (UI) (hereinafter, also referred to as a graphic user interface (GUI)) selectable by a user, and a display region in which a medical image is displayed. A user may open, i.e. load a medical image obtained by the medical apparatus such as the CT apparatus 101 through the UI in the input region of the application to, and the loaded medical image is provided to a user through the display region of the application. The displayed medical image includes a processed medical image for diagnosis.

According to one embodiment, the display region of the application may provide information (i.e. diagnosis information according to regions) about conditions of a predetermined anatomical entity (for example, a lung) included in the medical image.

According to one embodiment of the present invention, the image processing apparatus 100 may exchange medical image data with other medical apparatuses in hospital or hospital servers connected through a picture archiving and communication system (PACS). Further, the image processing apparatus 100 may perform data communication with a server or the like in accordance with standards of digital imaging and communications in medicine (DICOM).

According to one embodiment of the present invention, the image processing apparatus 100 may include a touch screen. The touch screen may be configured to detect not only a touch input position and a touched area, but also a touch input pressure. Further, the touch screen may be configured to detect a proximity touch as well as a real touch.

In this specification, the real touch refers to an input caused by real contact between a screen and a user's body (e.g. a finger) or a touch pen given as a touch tool (e.g. a pointing apparatus, a stylus, a haptic pen, an electronic pen, etc.). The proximity touch refers to an input caused by not real contact between a screen and a user's body or a touch tool but an approach up to a predetermined distance from the screen (e.g. hovering within a detectable distance of 30 mm or less).

The touch screen may be for example achieved by a resistive type, a capacitive type, an infrared type, or an acoustic wave type.

According to one embodiment of the present invention, the image processing apparatus 100 may sense a gesture input as a user's touch input to a medical image through the touch screen.

As a user's touch input to be described in this specification, there are a tap, a click stronger than the tap, touch and hold, a double tap, a double click, a drag corresponding to movement by a predetermined distance while keeping the touch, drag and drop, slide, flicking, panning, swipe, pinch, etc. The drag, slide, flicking, swipe, and the like input is divided into press corresponding to contact between the touch screen and a finger (or a touch pen), movement by a predetermined distance, and release from the touch screen, and includes all kinds of movement in the form of a straight line or a curved line. These various touch inputs are involved in the gesture input.

According to one embodiment of the present invention, the image processing apparatus 100 may provide some or all of buttons for controlling a medical image in the form a GUI.

Figure 2:
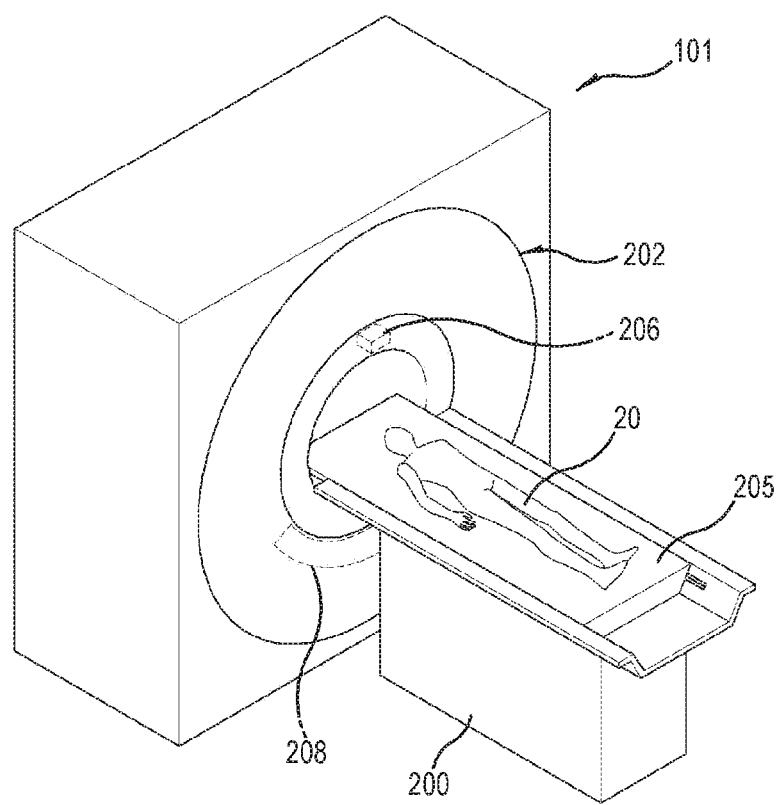
FIG. 2 is a view of showing a computed tomography (CT) apparatus as an image processing apparatus according to one embodiment of the present invention.
Figure 3:
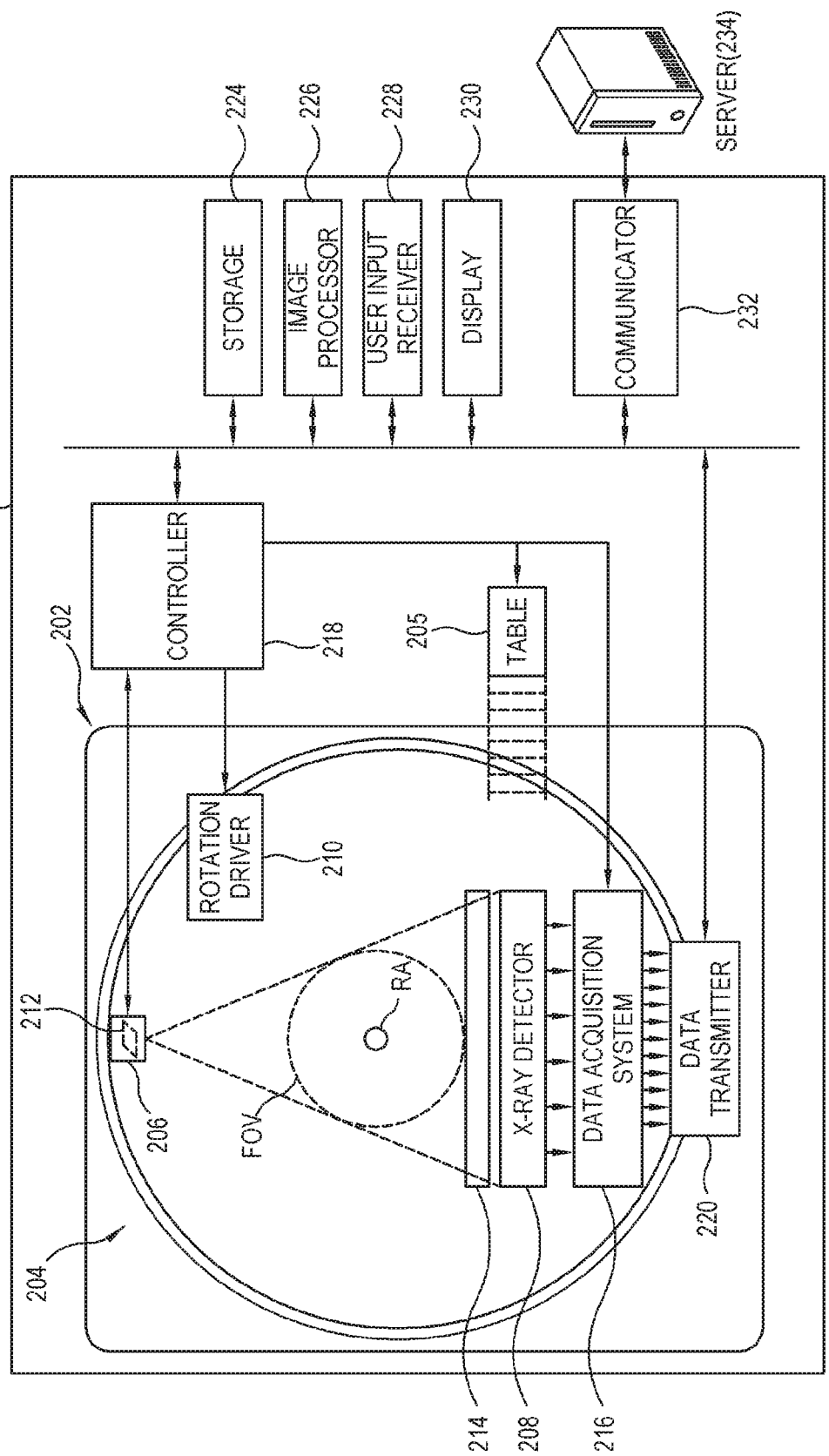
FIG. 3 is a view of schematically showing a configuration of the CT apparatus of FIG. 2.

FIG. 2 is a view of showing the CT apparatus 101 as the image processing apparatus 100 according to one embodiment of the present invention, and FIG. 3 is a view of schematically showing a configuration of the CT apparatus 101 of FIG. 2.

As shown in FIG. 2, the CT apparatus 101 may include a gantry 202, a table 205, an X-ray generator 206, and an X-ray detector 208.

Since the CT apparatus 101 and the like tomography apparatus can provide a cross-section image of the object, it is advantageous to show the internal structure (e.g. organs such as a kidney, a lung, etc. or muscles such as a diaphragm) of the object without overlapping as compared with general X-ray apparatuses.

The tomography apparatus may include all kinds of tomography apparatus such as the CT apparatus, an optical coherence tomography (OCT) apparatus, a positron emission tomography (PET)-CT apparatus, and the like.

In this embodiment, the tomography image is an image obtained by applying tomography to an object in the tomography apparatus, and may indicate an image obtained by using data projected after emitting an X-ray or the like beam to an object. Specifically, the CT image may refer to an image obtained by synthesizing a plurality of X-ray images obtained by photographing the object while rotating with respect to at least one axis of the object.

Below, as a tomography apparatus 200, the CT apparatus 101 shown in FIG. 2 and FIG. 3 will be described by way of example.

The CT apparatus 101 may provide a relatively accurate cross-section image with regard to an object by obtaining and processing tens or hundreds of images corresponding to a thickness of 2 mm or less per second. There is a conventional problem of showing only the transverse cross-section of the object, but this problem has been overcome by various image reconstruction techniques as follows. There are the imaging techniques for 3D reconstruction as follows.

Shade surface display (SSD): The early 3D imaging technique in which only voxels having a certain HU values are represented.

Maximum intensity projection (MIP)/minimum intensity projection (MinIP): The 3D technique of showing only voxels having the highest or lowest HU value among the voxels of forming the image.

Volume rendering (VR): The technique for adjusting color and penetrance of the voxels of forming the image according to interesting regions.

Virtual endoscopy: The technique in which a 3D image reconstructed by the VR or SSD technique is observed through endoscopy.

Multi planar reformation (MPR): The imaging technique for reconstruction with different cross-section images. The reconstruction is possible in a direction as desired by a user.

Editing: Various techniques for arranging surrounding voxels to more easily observe an interesting portion in the VR.

Voxel of interest (VOI): Technique for representing only a selected region with the VR.

The CT apparatus 101 according to one embodiment of the present invention will be described with reference to FIG. 2 and FIG. 3. The CT apparatus 101 according to one embodiment of the present invention may include various apparatuses as shown in FIG. 3.

The gantry 202 may include the X-ray generator 206 and the X-ray detector 208.

An object 20 may lie on the table 205.

During a CT process, the table 205 may move in a predetermined direction (for example, at least one of up, down, left and right directions). Further, the table 205 may be tilted or rotated at a predetermined angle in a predetermined direction.

Further, the gantry 202 may be tilted at a predetermined angle in a predetermined direction.

As shown in FIG. 3, The CT apparatus 101 according to one embodiment of the present invention may include the gantry 202, the table 205, the controller 218, a storage 224, an image processor 226, a user input receiver 228, a display 230, and a communicator 232.

As described above, the object 20 may lie on the table 205. The table 205 according to one embodiment of the present invention can move in a predetermined direction (for example, at least one of up, down, left and right directions), and may be controlled to move by the controller 218.

The gantry 202 according to one embodiment of the present invention may include a rotary frame 204, the X-ray generator 206, the X-ray detector 208, a rotation driver 210, a data acquisition circuit 216, and a data transmitter 220.

The gantry 202 according to one embodiment of the present invention may include the rotary frame 204 having a ring shape, which can be rotated with respect to a predetermined rotation axis (RA). Further, the rotary frame 204 may be shaped like a disc.

The rotary frame 204 may include the X-ray generator 206 and the X-ray detector 208, which are arranged to have a predetermined field of view (FOV). Further, the rotary frame 204 may include an anti-scatter grid 214. The anti-scatter grid 214 may be placed between the X-ray generator 206 and the X-ray detector 208.

In the CT apparatus 101, X-ray radiation, which reaches a detector (or a photosensitive film), may include not only attenuated primary radiation of forming a useful image but also scattered radiation or the like of deteriorating the quality of the image. To transmit most of primary radiation and attenuate the scattered radiation, the anti-scatter grid 214 may be arranged between a patient and the detector (or the photosensitive film).

For example, the anti-scatter grid may be structured by alternately stacking interspace materials such as strips of lead foil and a solid polymer material or a solid polymer and a fiber composite material. However, there are no limits to the foregoing structure of the anti-scatter grid.

The rotary frame 204 may rotate the X-ray generator 206 and the X-ray detector 208 at a predetermined rotating speed based on a driving signal received from the rotation driver

210. The rotary frame 204 may receive a driving signal and power from the rotation driver 210 by a contact method using a slip ring. Further, the rotary frame 204 may receive a driving signal and power from the rotation driver 210 through wireless communication.

The X-ray generator 206 receives voltage and current through a high-voltage generator (not shown) via the slip ring (not shown) from a power distribution unit (PDU, not shown) and generates and emits an X-ray. When the high-voltage generator applies a predetermined voltage (hereinafter, referred to as a tube voltage), the X-ray generator 206 can generate X-rays having a plurality of energy spectra corresponding to such a predetermined tube voltage.

The X-ray generated by the X-ray generator 206 may be emitted in a predetermined form by a collimator 212.

The X-ray detector 208 may be placed facing the X-ray generator 206. The X-ray detector 208 may include a plurality of X-ray detecting elements. The single X-ray detecting element may form a single channel, but is not limited thereto.

The X-ray detector 208 senses the X-ray generated by the X-ray generator 206 and received via the object 20, and generates an electric signal corresponding to the intensity of the sensed X-ray.

The X-ray detector 208 may include an indirect detector that detects light converted from radiation, and a direct detector that detects electric charges converted from the radiation. The indirect X-ray detector may employ a scintillator. Further, the direct X-ray detector may employ a photon counting detector. The data acquisition system (DAS) 216 may be connected to the X-ray detector 208. The electric signal generated by the X-ray detector 208 may be collected in the DAS 216. The electric signal generated by the X-ray detector 208 may be collected in the DAS 216 by a wire or wirelessly. Further, the electric signal generated by the X-ray detector 208 may be provided to an analog/digital converter (not shown) via an amplifier (not shown).

Only some pieces of data collected from the X-ray detector 208 may be provided to the image processor 226 in accordance with slice thickness or the number of slices, or the image processor 226 may select only some pieces of data.

Such a digital signal may be transmitted, i.e. provided to the image processor 226 through the data transmitter 220 by a wire or wirelessly.

The controller 218 of the CT apparatus 101 according to one embodiment of the present invention may control operations of modules in the CT apparatus 101. For example, the controller 218 may control the operations of the table 205, the rotation driver 210, the collimator 212, the DAS 216, the storage 224, the image processor 226, the user input receiver 228, the display 230, the communicator 232, etc.

The image processor 226 receives data (e.g. pure data before process) acquired from the DAS 216 through the data transmitter 220, and performs a pre-processing process.

The pre-processing process may for example include a correction process for sensitivity inhomogeneity between channels, a correction process for signal loss due to sudden decrease in signal strength or an X-ray absorbing material such as metal, etc.

The output data of the image processor 226 may be called raw data or projection data. The projection data may be stored together with image-taking conditions (e.g. a tube voltage, an image-taking angle, etc.) for obtaining data in the storage 224.

The projection data may be a set of data values corresponding to the intensity of the X-ray passed through the object. For convenience of description, a set of projection data simultaneously obtained at the same image-taking angle with regard to all channels will be called a projection data set.

The storage 224 may include at least one type of storage media such as a flash memory type, a hard disk type, a multimedia card micro type, a card type memory (an SD, XD and the like memories), a random access memory (RAM), a static random access memory (SRAM), a read-only memory (ROM), an electrically erasable programmable read-only memory (EEPROM), a programmable read-only memory (PROM), a magnetic memory, a magnetic disk, and an optical disc.

Further, the image processor 226 may use the acquired projection data set to reconstruct a cross-section image of an image. The cross-section image may be a 3D image. In other words, the image processor 226 may generate a 3D image of the object by using a cone beam reconstruction method or the like based on the acquired projection data set.

Through the user input receiver 228, an external input about an X-ray tomography condition, an image processing condition, etc. may be received. For example, the X-ray tomography condition may include a plurality of tube voltages, energy level settings for a plurality of X-rays, selection of a tomography protocol, selection of the image reconstruction method, settings for an FOV region, the number of slices, slice thickness, settings for image post-processing parameters, etc. Further, the image processing condition may include a resolution of an image, attenuation coefficient settings for the image, combination ratio settings for the image, etc.

The user input receiver 228 may include an apparatus or the like for receiving a predetermined input from the outside. For example, the user input receiver 228 may include a microphone, a keyboard, a mouse, a joystick, a touch pad, a touch pen, voice and gesture recognition apparatuses, etc.

The display 230 may display an X-ray tomography image reconstructed by the image processor 226.

The data, power, etc. may be transceived between the foregoing elements by at least one of wired, wireless and optical communications. For example, a high-speed digital interface such as low voltage differential signaling (LVDS), etc.; asynchronous serial communication such as a universal asynchronous receiver transmitter (UART), etc.; false synchronization serial communication; a low-delay network protocol such as a controller area network (CAN), etc.; or optical communication; etc. may be used, and other various communication methods may be employed as long as they are obvious to a person having an ordinary skill in the art. Further, in a case of connection using the wireless communication, a device (not shown) for synchronizing clocks between them may be further provided.

The communicator 232 may communicate with an external apparatus, other external medical apparatuses, etc. through a server 234.

Figure 4:
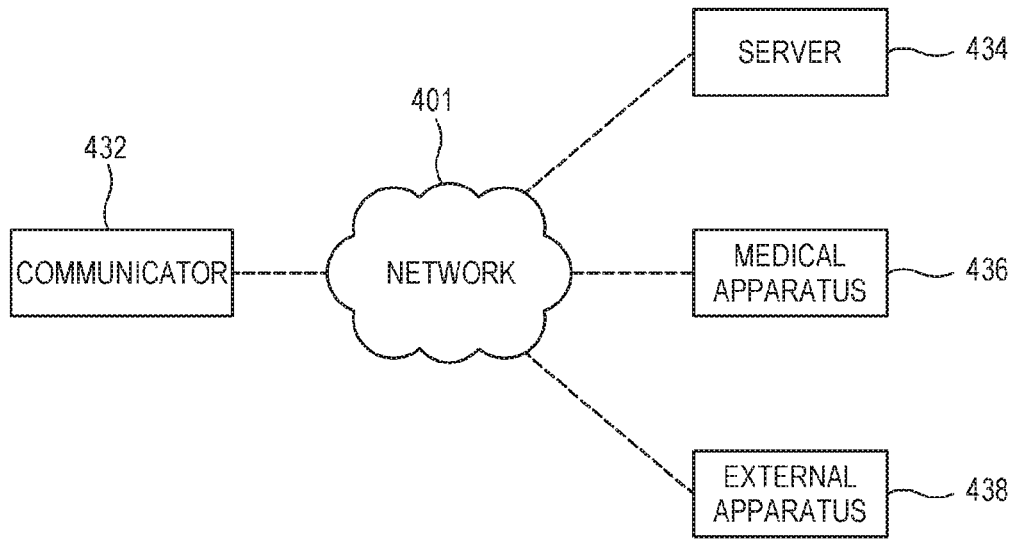
FIG. 4 is a view of schematically showing a configuration of a communicator to communicate with the outside in a network system.

FIG. 4 is a view of schematically showing a configuration of a communicator 432 allowing the image processing apparatus 100 to communicate with the outside in a network system.

According to one embodiment, as shown in FIG. 4, the communicator 432 connects with a wired or wireless network 401 and performs communication with an external server 434, other external medical apparatus 436, or an external apparatus 438.

For example, the communicator 432 may transmit and receive data related to diagnosis of an object through the network 401, and may also transmit and receive an medical image taken by the CT, ultrasound, X-ray and the like other medical apparatuses 436.

According to one embodiment, the communicator 432 shown in FIG. 4 may be included in the CD apparatus 101 of FIGS. 2 and 3. In this case, the communicator 432 shown in FIG. 4 is equivalent to the communicator 232 shown in FIG. 3. Further, other medical apparatuses 436 may for example be an MRI apparatus or an ultrasound apparatus capable of providing a medical image.

Detailed operations of the communicator 432 are as follows.

The communicator 432 may connect with the wired or wireless network 401 and perform communication with a server 434, an external medical apparatus 436 or an external apparatus 438. The communicator 432 may exchange data with a hospital server connected through the PACS or other medical apparatuses in the hospital. Further, the communicator 432 may perform data communication with the external apparatus 438 or the like in accordance with the DICOM standards.

The communicator 432 may transmit and receive an image of an object and/or data related to diagnosis of the object through the network 401. The communicator 432 may receive the medical image or the like obtained in the MRI apparatus, the X-ray apparatus, and the like other medical apparatuses 436.

Besides, the communicator 432 may receive a diagnosis history, a care schedule, etc. of a patient from the server 434, and utilize them in a patient's clinic diagnosis or the like. Further, the communicator 432 may perform data communication with not only the server 434 or the medical apparatuses 436 in the hospital, but also an external apparatus 438 including a portable apparatus (terminal) of a user or patient.

Further, defects in equipment and quality control information are transmitted to a system administrator or service representative though the network, and get a feedback on them.

According to one embodiment, the image processing apparatus 100 may receive information, i.e. data about a predetermined anatomical entity from the server 434 through the communicator 432. The image processing apparatus 100 may be configured to build a standard database (DB) about a predetermined anatomical entity based on the data received therein, and provide information about the conditions of the corresponding anatomical entity based on the standard DB. According to another embodiment, the standard DB may be established in the external apparatus including the server 434, and the image processing apparatus 100 may be configured to receive information needed for providing the conditions of the anatomical entity from the standard database of the external apparatus through the communicator 432.

The medical images show the object in various ways in accordance with the kinds/diagnostic purposes, etc. of medical apparatus. Further, the features of the obtained medical image may be processed to be varied depending on the kinds/diagnostic purposes of medical apparatus. For example, a certain medical image makes it easy to grasp cancer tissues, and another medical image makes it easy to grasp a blood vessel.

Therefore, there is a need of providing a medical image processed suitably for a user's intention by taking a portion to be read out from an image into account.

Below, the image processing apparatuses according to one or other embodiments of the present invention, which can process and provide a medical image for facilitating a user's diagnosis with regard to a predetermined region in the medical image to the user, will be described in detail with reference to the accompanying drawings.

The image processing apparatuses 100 according to one or other embodiments of the present invention may include any image processing apparatus capable of displaying, storing and/or processing the medical image.

Specifically, the image processing apparatus 100 according to one embodiment of the present invention may be included in the CT apparatus 101 as the medical apparatus described with reference to FIGS. 2 and 3. For example, the image processing apparatus 100 may process the obtained medical image and provide it to a user through the display 230 of FIG. 3.

Further, the image processing apparatus 100 according to another embodiment of the present invention may be the server 534 connected to at least one medical apparatus such as the CT apparatus described with reference to FIGS. 2 and 3 through the network 501, or may be the display apparatus 102 of FIG. 1. Here, the image processing apparatus 100 may be included in the PACS capable of displaying, storing or processing at least one of various medical images.

Further, the image processing apparatus 100 according to another embodiment of the present invention may be included in any medical image apparatus/system for processing/recovering an image based on data obtained by scanning an object, as well as the CT apparatus 101, or may be connected to any medical image apparatus/system.

Figure 5:
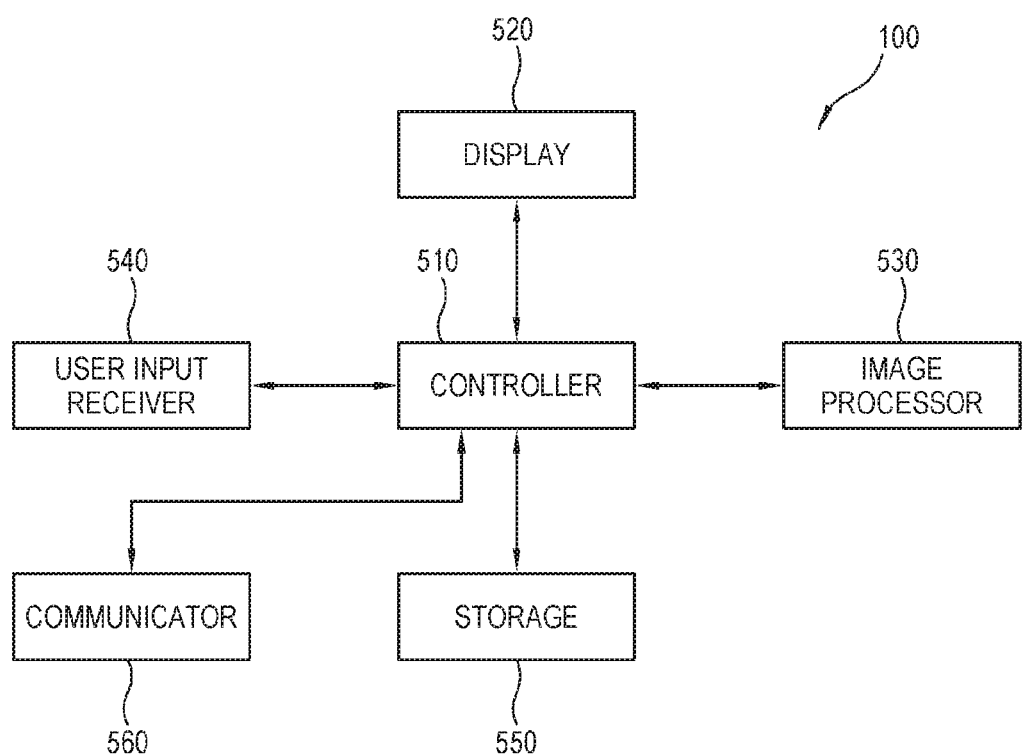
FIG. 5 is a block diagram of showing a configuration of an image processing apparatus according to one embodiment of the present invention.

FIG. 5 is a block diagram of showing a configuration of the image processing apparatus 100 according to one embodiment of the present invention.

As shown in FIG. 5, the image processing apparatus 100 according to one embodiment of the present invention includes a controller 510, a display 520, an image processor 530, a user input receiver 540, a storage 550 and a communicator 560. However, all the illustrated elements are not essential, and other general-purpose elements may be further provided in addition to the illustrated elements.

When the image processing apparatus 100 is included in the CT apparatus 101 shown in FIGS. 2 and 3, the controller 510, the display 520, the image processor 530, the user input receiver 540 and the storage 550 may correspond to the controller 218, the display 230, the image processor 226, the user input receiver 228 and the storage 224 of FIG. 3, respectively. Therefore, repetitive descriptions of the image processing apparatus 100 with regard to those of FIG. 2 or FIG. 3 will be avoided.

The display 520 displays an application related to operations of the image processing apparatus 100. For example, the display 520 may display a menu or a guide needed in diagnosis using the medical apparatus. Further, the display 520 may display an image obtained during the diagnosis, and a user interface (UI) for helping a user to control the medical image processing apparatus.

FIG. 5 shows an example that one display 520 is provided in the image processing apparatus 100, but the present invention is not limited thereto. Alternatively, the image processing apparatus 100 may be configured to include a plurality of displays, for example, a main display and a sub display.

In this embodiment, the display 520 may display a first image (or a first medical image) and a second image (or a second medical image) obtained by scanning an object including at least one anatomical entity, and may further display a third image (or a third medical image) produced by registering the first image and the second image.

According to one embodiment, the display 520 may normalize the local motion vector, which is obtained by the registration of the first and second images based on the predictive local motion vector generated using the information of the standard database stored in the storage 550 (to be described later), according to a plurality of regions of a predetermined anatomical entity, and provide the information about the conditions of the anatomical entity, i.e. the diagnosis information based on the normalized local motion vector according to the plurality of regions. Here, the display 520 may further display a fourth image (or a fourth medical image) for providing the diagnosis information about the anatomical entity according to the plurality of regions.

Here, the first image and the second image may for example the pulmonary CT images as the medical images obtained by scanning the object including a predetermined anatomical entity. When the first image and the second image are the pulmonary CT images, the first image may correspond to an inspiratory image and the second image may correspond to an expiratory image.

Meanwhile, the medical image of the present invention is not limited to the CT image, and may include any medical image taken for diagnosis of diseases, such as an MRI image or the like tomography image, an X-ray image, an ultrasound image, etc.

The image processor 530 processes the image to be displayed on the display 520. Specifically, the image processor 530 processes a signal obtained by scanning the object into an image to be displayable on the display 520.

As an imaging method of the medical image, there is a method of taking an image of an object by emitting a beam such as an X-ray to the object like the X-ray imaging method. This imaging method is performed without separating an image-taking mode and a scanning mode. Further, this imaging method can directly take an image of an object without separately performing restoration or calculation for the image desired to be obtained.

There is another method of taking an image of an object by variously applying the image-taking mode or the scanning mode like an MRI or CT image. In this case, using various parameters that can be considered while scanning the object, it is possible to obtain images different in characteristic even though the images are obtained by photographing the same part of the body. That is, it is possible to obtain an image suitable for a purpose by changing the scanning mode in accordance with usage or purposes. Further, this imaging method can obtain a desired image by separately performing restoration or calculation for the image desired to be obtained.

Here, the technique used in taking a medical image by scanning an object is called a 'scan protocol' or a 'protocol'. Below, the 'protocol' will be used. Further, the image processor 530 may generate a medical image by applying a predetermined protocol to obtained image data.

According to one embodiment of the present invention, the image processor 530 may generate calculated or post-processed image data (i.e. the third image or the fourth image), using the image data (i.e. the first image or the second image) obtained by applying the protocol. In this embodiment, the calculation or post-process may include image registration, entity segmentation, vector operation in a segmented entity region, calculation of indexes indicating information about entity conditions, etc.

The CT apparatus 101 scans an object by applying different protocols in accordance with whether the contrast media is injected or not. Further, the image data obtained by the CT apparatus 101 may become sinogram or projection data, and the image data, i.e. the first and second images may be generated using the obtained scan data.

The user input receiver 540 is provided to receive a command from a user. The image processing apparatus 100 in this embodiment receives a user's input for controlling the image processing apparatus 100 through the user input receiver 540, and outputs the first medical image, the second medical image, the third medical image and/or the fourth medical image obtained by the image processing apparatus 100 through the display 520 in response to the received input.

The user input receiver 540 may include a button, a keypad, a switch, a dial or a user interface displayed on the display 520 for allowing a user to directly control the image processing apparatus 100. According to one embodiment of the present invention, the user input receiver 540 may include a touch screen provided on the display 520. When the user input receiver 540 includes the touch screen, the display 520 may provide information about an entity corresponding to a point selected by a user in the displayed medical image, or enlarge and display the selected point.

The storage 550 stores data without limitations under control of the controller 510. The storage 550 may be materialized by a flash memory, a hard disc drive or the like nonvolatile storage medium. The storage 550 is accessed by the controller 510, and thus the controller 510 is capable of reading/recording/modifying/deleting/updating the data.

The data stored in the storage 550 may for example include not only an operating system for driving the image processing apparatus 100, but also various applications executable in this operating system, image data, appended data, etc.

The storage 550 in this embodiment may be configured to store various pieces of data for providing information about a predetermined anatomical entity. Specifically, the storage 550 is configured to store at least one piece of medical image data generated by applying at least one protocol in the image processing apparatus 100, and/or at least one piece of medical image data received from the outside. The image data stored in the storage 550 can be displayed by the display 520. Further, the image data stored in the storage 550 may be at least one among the first medical image, the second medical image, the third medical image and the fourth medical image according to one embodiment of the present invention.

Further, the storage 550 may include the standard database established by collecting pieces of information about at least one anatomical entity. The standard database may be utilized in generating the predictive local motion vector (to be described later). The standard database may be built by vectorizing a plurality of medical images about a predetermined anatomical entity (e.g. a lung), and applying statistical modeling to the vectorized data.

The communicator 560 includes a wired/wireless network communication module for performing communication with various external apparatuses. The communicator 560 transmits a command/data/information/signal received from the outside to the controller 510. Further, the communicator 560 may transmit a command/data/information/signal received from the controller 510 to the external apparatus.

According to this embodiment, the communicator 560 is internally provided in the image processing apparatus 100. However, according to one embodiment, the communicator may be materialized in the form of a dongle or a module and detachably connected to a connector (not shown) of the image processing apparatus 100.

According to another embodiment, the communicator 560 may include an input/output (I/O) port for connecting with human interface apparatuses (HID). The image processing apparatus 100 may use the I/O port to exchange the image data with an external apparatus.

The communicator 560 in this embodiment may receive medical image data generated in another medical apparatus. Here, another medical apparatus may include various kinds of medical apparatus. For example, another medical apparatus may include a CT apparatus. Optionally, another medical apparatus may include an MRI apparatus or an ultrasound apparatus.

In one embodiment, the image processing apparatus 100 may be directly connected to another medical apparatus through the communicator 560. According to another embodiment, the communicator 560 may further include a connector for connecting with an external storage medium in which the medical image is stored.

The controller 510 controls various elements of the image processing apparatus 100. For example, the controller 510 performs a process related to an imaging process/entity segmentation/vector operation, etc. of the image processor 530, and performs a control corresponding to a command from the user input receiver 540, thereby controlling general operations of the image processing apparatus 100.

The controller 510 includes at least one processor. At least one processor loads a program from a nonvolatile memory (e.g. ROM) storing the program to a volatile memory (e.g. RAM), and executes the program.

The controller 510 according to this embodiment includes at least one general-purpose processor such as a central processing unit (CPU), an application processor (AP), and a microcomputer (MICOM), and loads and executes a program corresponding to a predetermined algorithm from the ROM to the RAM, thereby implementing various operations of the image processing apparatus 100.

When the controller 510 of the image processing apparatus 100 is materialized as a single processor, e.g. a CPU, the CPU may be provided to implement various functions performable in the image processing apparatus 100, such as various image processing processes for the medical image to be displayed on the display 520, for example, selection of a protocol to be applied, imaging control corresponding to the selected protocol, following a command received through the user input receiver 540, control of wired/wireless network communication with an external apparatus, etc.

The processor may include a single-core processor, a dual-core processor, a triple-core processor, a quad-core processor, and the like multiple-core processor. The processor may include a plurality of processors, for example, a main processor and a sub processor. The sub processor is provided to operate in a standby mode (hereinafter, referred to as a sleep mode) in which it is supplied with only standby power and does not operate as the image processing apparatus 100.

The processor, the ROM and the RAM included in the controller 510 may be connected to one another by an internal bus.

According to one embodiment of the present invention, when the image processing apparatus 100 is materialized by a laptop or desktop computer, the controller 510 may further include a graphic processing unit (GPU, not shown) provided for a graphic process in a main body. Further, according to another embodiment, when the image processing apparatus 100 is materialized by a portable terminal such as a smart phone, a smart pad, etc., the processor may include a GPU. For example, the processor may be materialized by a system on chip (SoC) where the core and the GPU are coupled.

Further, the controller 510 may include a program for performing a specific function supported in the image processing apparatus 100, for example, a function for sensing an error in a predetermined element including the main processor, and a chip provided as a dedicated processor for executing the program, for example, an integrated chip (IC).

In one embodiment, the controller 510 may receive a user command for executing a predetermined application as a platform capable of analyzing the medical image through the user input receiver 540 or making a diagnosis using the same. The executed application may include an input region in which various buttons are displayed as an UI for a user' selection, and a display region in which the medical image is displayed.

A user can use the UI of the input region of the application to open, i.e. load the medial image stored in the inside or the outside, and the loaded medical image is displayed on the display 520 through the display region of the application. Further, a user may input a user command for making the executed application provide information about a predetermined anatomical entity.

According to one embodiment of the present invention, the image processor 530 may be materialized by a medical image analysis application, i.e. software to be driven by the controller 510 including at least one processor as a hardware.

That is, the operations of the image processor 530 to be described below are implemented by execution of software to be driven by the controller 510. Therefore, it may be regarded that various operations performed in the image processor 530 are implemented by the controller 510, that is, at least one processor.

Below, first to third embodiments of providing information about conditions of an anatomical entity to be subjected to a diagnosis, i.e. a lung through a thoracic image, i.e. a pulmonary CT image used as the medical image will be described in more detail.

However, the following descriptions are related to realizable embodiments of the present invention, and do not limit the present invention. For example, the image processing apparatus 100 according to the present invention may use not only a CT image but also an MRI image to provide information about conditions of a predetermined anatomical entity such as a lung. Further, the anatomical entity, information about which will be provided, is not limited to the lung, but the information may be utilized in diagnosing organs such as a stomach, a heart, a brain, etc. or tissues such as muscles.

The controller 510 of the image processing apparatus 100 according to the first embodiment of the present invention extracts regions corresponding to a predetermined anatomical entity to be subjected to a diagnosis from a first medical image and a second medical image obtained by scanning an object including a plurality of anatomical entities, and registers the first medical image and the second medical image, from which the regions are extracted, thereby producing a third medical image. Here, the controller 510 may obtain a local motion vector defined as a kind of displacement vector during image registration.

The controller 510 uses the predictive local motion vector produced from the standard database stored in the storage 550 to normalize the local motion vector acquired during the image registration according to a plurality of regions configuring the anatomical entity to be subjected to the diagnosis. Further, the controller 510 analyzes the conditions of the anatomical entity to be subjected to the diagnosis according to the plurality of regions based on the normalized local motion vector, and provides the information according to the plurality of regions. Here, the controller 510 may control the display 520 to provide the information about the conditions of the anatomical entity to be diagnosed according to the plurality of regions.

Here, the object may be an entire or partial body of a patient, for example, a chest. Therefore, the medical image obtained by scanning the object according to one embodiment of the present invention may be a thoracic image, more specifically, a respiratory CT image (or a pulmonary CT image). The respiratory CT image may include a plurality of anatomical entities, for example, other organs such as a diaphragm, a rib cage including ribs, etc. in addition to the lung.

Further, the plurality of regions in the lung are lobes of the lungs, in which the right lung is segmented into three regions of an upper lobe, a middle lobe and a lower lobe, and the left lung is segmented into two regions of an upper lobe and a lower lobe. The controller 510 finds a pulmonary fissure in the regions of the lungs, and controls the display 520 to provide an image in which the lungs can be diagnosed in units of lobes.

FIGS. 6 to 14 are views for showing a process for providing information about conditions of a predetermined anatomical entity in the image processing apparatus 100 according to the first embodiment of the present invention.

Figure 6:
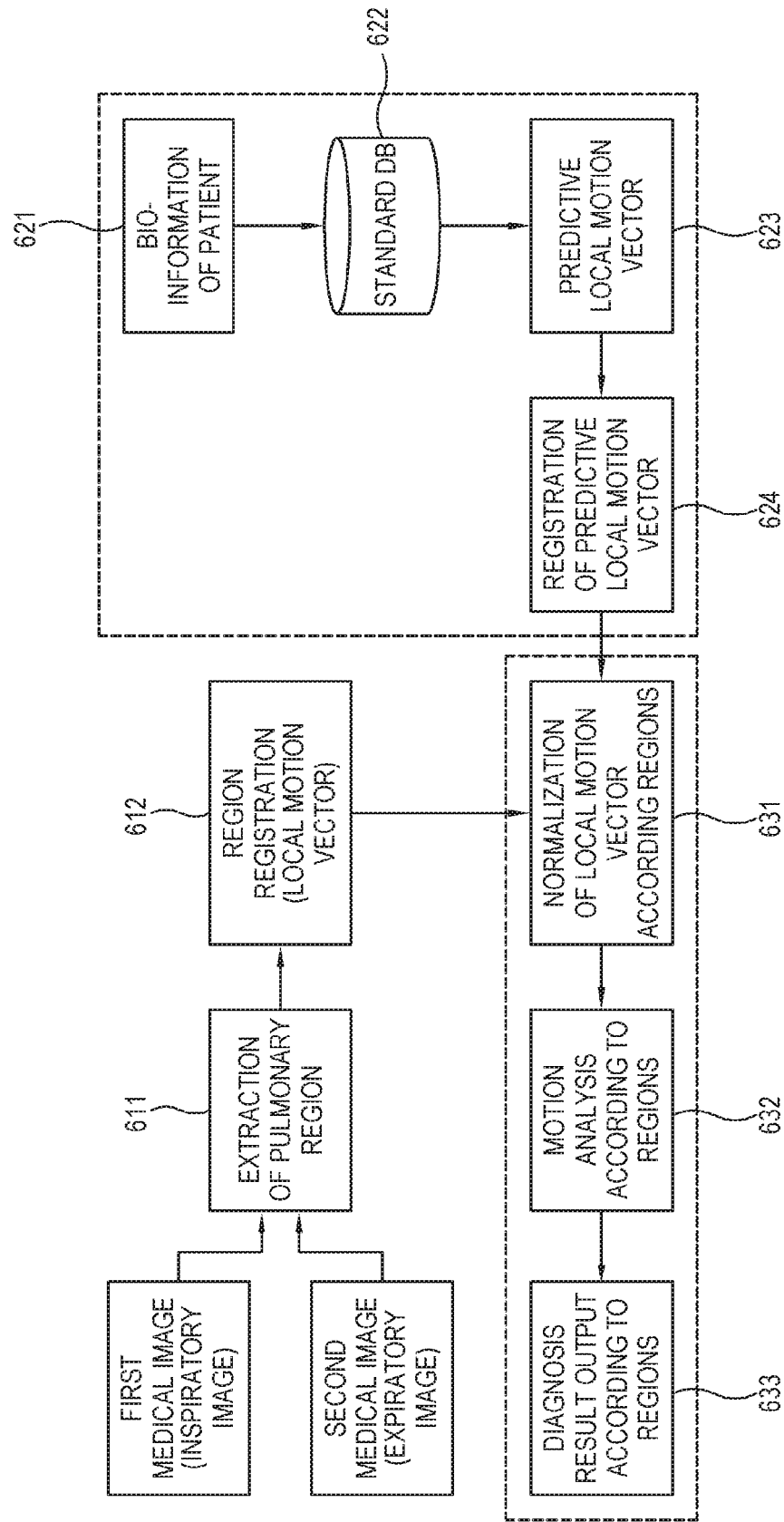

In the first embodiment, the image processing apparatus 100 as shown in FIG. 6 detects/segments the pulmonary region from the scanned respiratory CT images, i.e. an inspiratory image (or CT inspiration data) and an expiratory image (or CT expiration data) (lung segmentation) (611), and applies image registration to the segmented pulmonary region (lung registration). The controller 510 may acquire the local motion vector during this registration process (612).

Here, the respiratory CT image may be an image currently taken by the CT apparatus or an image previously taken for the purpose of a different diagnosis as necessary. Referring to FIG. 7, the respiratory CT image in this embodiment includes an inhale or inspiratory image 701 defined as the first medical image, and an exhale or expulsive image 702 defined as the second medical image.

Figure 8:
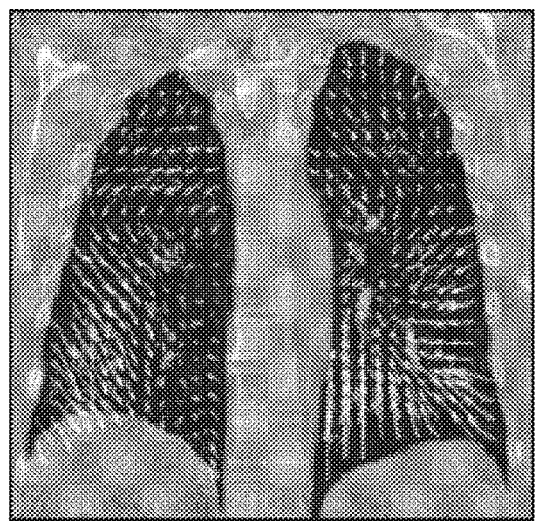

The local motion vector corresponds to a displacement vector calculated during the image registration of the lungs performed by the controller 510. The controller 510 may control the display 520 { 도면에 없습니다 } to display the local motion vector calculated with regard to the pulmonary region. FIG. 8 illustrates an example that the local motion vector computed in the pulmonary region is displayed through the display 520.

In the image processing apparatus 100 according to the first embodiment, the standard DB established with data collected with regard to an anatomical entity to be subjected to a diagnosis (for example, the lung). Here, the collected data includes a plurality of medical images including the anatomical entity to be subjected to the diagnosis, and attribute information matching with the corresponding medical image (for example, metadata). According to one embodiment, the attribute information may for example include at least one of physical features, biological features, and habitual features, as bio-information Bio Info about an object to be taken as a corresponding medical image. The physical features include height, weight, etc. of an object to be scanned; the biological features include age, sex, etc.; and the habitual features include smoking, respiratory allergy, etc.

According to one embodiment, an object to be scanned for establishing the standard DB may be a normal person as a concept distinguishable from a patient who has or is suspected of having a pulmonary disease. Therefore, the medical images in the standard DB may include the respiratory CT images of normal people having normal lungs.

According to another embodiment, an object to be scanned for establishing the standard DB may be a normal person as a concept including a patient who has or is suspected of having a pulmonary disease. Therefore, the medical images in the standard DB may include the respiratory CT images of people (e.g. Korean over 20 years old under 60 years old) who belong to a certain group regardless of the pulmonary disease.

Figure 9:
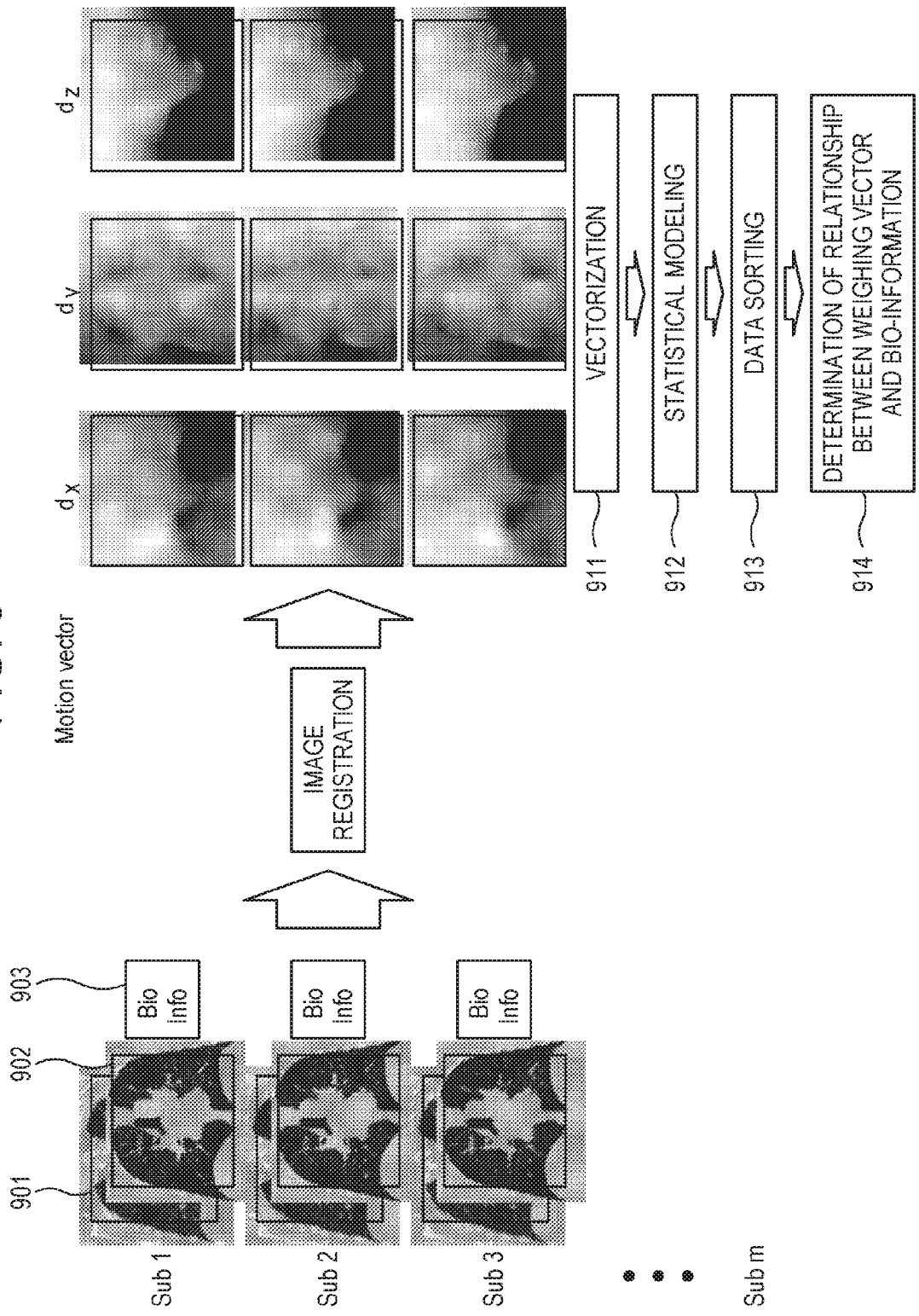

FIG. 9 is a view of showing a process for building a standard DB in the image processing apparatus 100 according to the first embodiment of the present invention.

As shown in FIG. 9, the controller 510 collects a plurality of medical images Sub 1, Sub 2, Sub 3 . . . Sub m as data (normal subject) including the anatomical entity to be subjected to the diagnosis, i.e. the lung, together with the bio-information Bio Info matching with the medical images. Here, the collected medical images include the inspiratory image and the expiratory image. For example, in a case of a first subject Sub 1 defined as a respiratory CT image of a certain normal person, the inspiratory image 901 and the expiratory image 902 as the respiratory CT image may be collected together with their bio-information 903.

The controller 510 performs registration of medical images with respect to each subject. Here, the image registration may include registration between the inspiratory image and the expiratory image (Insp-Exp Registration), and may further include image registration based on a predetermined registration algorithm (for example, affine and non-rigid registration or atlas registration).

In the process of the image registration, as shown in FIG. 9, the controller 510 may acquire motion vectors dx, dy and dz having predetermined directivity with respect to each subject. In this embodiment, this process is defined as vectorization 911, and the controller 710 vectorizes the collected medical images according to the subjects.

The controller 510 applies statistical modeling of a predetermined method to the vectorized data (912). Here, as shown in FIG. 9, the statistical modeling may for example employ one among principal component analysis (PCA), discrete Karhunen-Loéve transform (KLT), singular value decomposition (SVD), eigen value decomposition (EVD), and empirical orthogonal function (EOF) as decomposition modeling.

As above, the vector data subjected to the statistical modeling is changed into a weighting vector, and the controller 510 sorts components by a predetermined reference (component sorting)(913). Further, a relationship between a weighted value assigned to the sorted vector data (B/W component) and the bio-information matched to the corresponding medical image is found (find relationship b/w comp. weighting and bio info), thereby building the standard DB. In this process, a regression analysis may be used.

Figure 10:
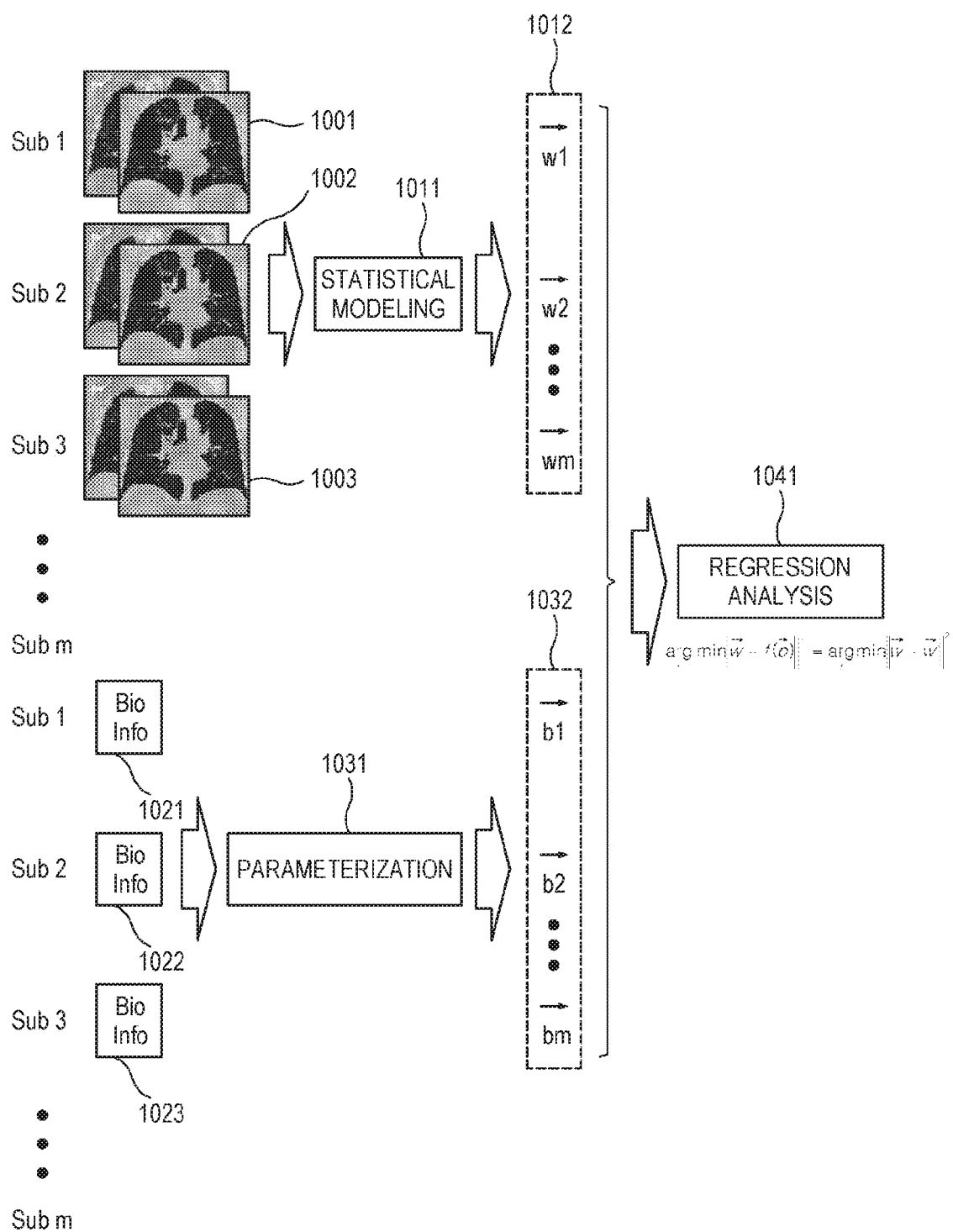

FIG. 10 is a view of showing a process for finding a relationship between the vector data and the bio-information to establish the standard DB of FIG. 9.

As shown in FIG. 10, the controller 510 may obtain vector data $\vec{w}_1, \vec{w}_2 \ldots, \vec{w}_m$ (1012) by applying the statistical modeling (1011) to the plurality of medical images Sub 1, Sub 2, Sub 3, . . . , Sub m (1001, 1002, 1003).

Further, the bio-information Bio info. (1021, 1022, 1023) matched to each image is parameterized (1031), to thereby obtain vector data $\vec{b}_1, \vec{b}_2, \ldots, \vec{b}_m$ (1032).

The controller 510 performs the regression analysis with regard to the obtained vector data as shown in FIG. 10, thereby finding the relationship between the vector data. In this process, the following expression 1 may be used.

$$\underset{f}{\operatorname{argmin}} \|\vec{w} - f(\vec{b})\|^2 = \underset{f}{\operatorname{argmin}} \|\vec{w} - \vec{w}'\|^2 \quad \text{[Expression 1]}$$

$\vec{w}_i$=Decomposition weighting vector of i-th subject
$\vec{b}_i$=Bio vector of i-th subject
$\vec{w}$=Decomposition weighting vector
$\vec{w}'$=Weighting vector estimated by regression analysis
f=Regression function Here, as an example of a regression function used in the regression analysis, a linear regression algorithm may be employed. The following expression 2 shows the linear regression algorithm used according to one embodiment of the present invention.

$$a_1 b_1^1 + a_2 b_2^1 + \ldots + a_m b_m^1 = w_1^1 \quad \text{[Expression 2]}$$
$$a_1 b_1^2 + a_2 b_2^2 + \ldots + a_m b_m^2 = w_1^2$$
$$\ldots$$
$$a_1 b_1^n + a_2 b_2^n + \ldots + a_m b_m^n = w_1^n$$

$$\begin{bmatrix} b_1^1 & b_2^1 & \ldots & b_m^1 \\ b_1^2 & b_2^2 & \ldots & b_m^2 \\ \ldots & \ldots & \ldots & \ldots \\ b_1^n & b_2^n & \ldots & b_m^n \end{bmatrix} \begin{bmatrix} a_1 \\ a_2 \\ \ldots \\ a_m \end{bmatrix} = \begin{bmatrix} w_1^1 \\ w_1^2 \\ \ldots \\ w_1^n \end{bmatrix}$$

$$B \cdot \vec{a} = \vec{w}$$
$$\vec{a} = (B^T B)^{-1} B^T \vec{w}$$

$a_i$=i-th coefficient of linear model associated with $w_1$ (i=1, . . . m)
$b_i^j$=i-th biovariable of j-th subject (i=1, . . . , m, j=1, . . . , n)
$w_i^j$=i-th weight of j-th subject (1, . . . , m, j=1, . . . , n)

This process is repeated to obtain the linear model w. r. to the r $w_i$

In result, the controller 510 builds the standard DB with the motion vectors mathematically computed based on the bio-information and the vector data corresponding to each subject. The standard DB may be stored by statistically averaging the motion vectors, and may be stored by sorting a series of motion vectors having similar features in units of group as necessary. According to one embodiment, the standard DB is also called statistical atlas.

Referring to FIG. 6, the controller 510 receives bio-information of a patient to be subjected to a diagnosis (621), and finds a predictive local motion vector model for the patient from the standard DB 622 established as above (623). In this embodiment, the image processing apparatus 100 may employs various expressions/algorithms in finding the predictive local motion vector.

According to one embodiment, the controller 510 may find the predictive local motion vector by applying a mathematical operation derived from the statistical modeling described in the process of building the standard DB of FIGS. 9 and 10 to the bio-information of the patient. In this process, the following expression 3 is used.

$$d_x(x, y, z) = \tilde{f}_x(x, y, z, \text{biovariables}) = \quad \text{[Expression 3]}$$
$$V_{x,0} + \sum_{i=1}^{k} w_i(\text{biovariables}) V_{x,i}(x, y, z)$$

$$d_y(x, y, z) = \tilde{f}_y(x, y, z, \text{biovariables}) =$$
$$V_{y,0} + \sum_{i=1}^{k} w_i(\text{biovariables}) V_{y,i}(x, y, z)$$

$$d_z(x, y, z) = \tilde{f}_z(x, y, z, \text{biovariables}) =$$
$$V_{z,0} + \sum_{i=1}^{k} w_i(\text{biovariables}) V_{z,i}(x, y, z)$$

$d_x, d_y, d_z$=Estimated motion vectors for normal subject in x, y, and z directions
$\tilde{f}_x, \tilde{f}_y, \tilde{f}_z$=Mathematical decomposition models in x, y, and directions
(Orthogonal transformation-based: PCA, KLT, SVD, EVD, EOF, etc.
$w_i$=i-th weight
$v_{x,i}, v_{y,i}, v_{z,i}$=i-th decomposed motion vectors in x, y, and z directions
$v_{z,0}, v_{y,0}, v_{z,0}$=Mean motion vectors in x, y, and z directions In the expression 3, the function applied to each vector data of a predetermined direction may correspond to the statistical model (e.g. decomposition model) described in relation to the standard DB, and may for example be the orthogonal transform based on one of PCA, KLT, SVD, EVD and EOF.

The controller 510 finds the motion vectors dx, dy and dz, which are calculated by the Expression 3 corresponding to the bio-information (or bio variables) of the patient to be subjected to the diagnosis, as the predictive local motion vector.

According to another embodiment, the controller 510 may select the motion vector, which is the most similar to the bio-information of the patient to be subjected to the diagnosis based on search from the standard DB, as the predictive local motion vector.

Figure 11:
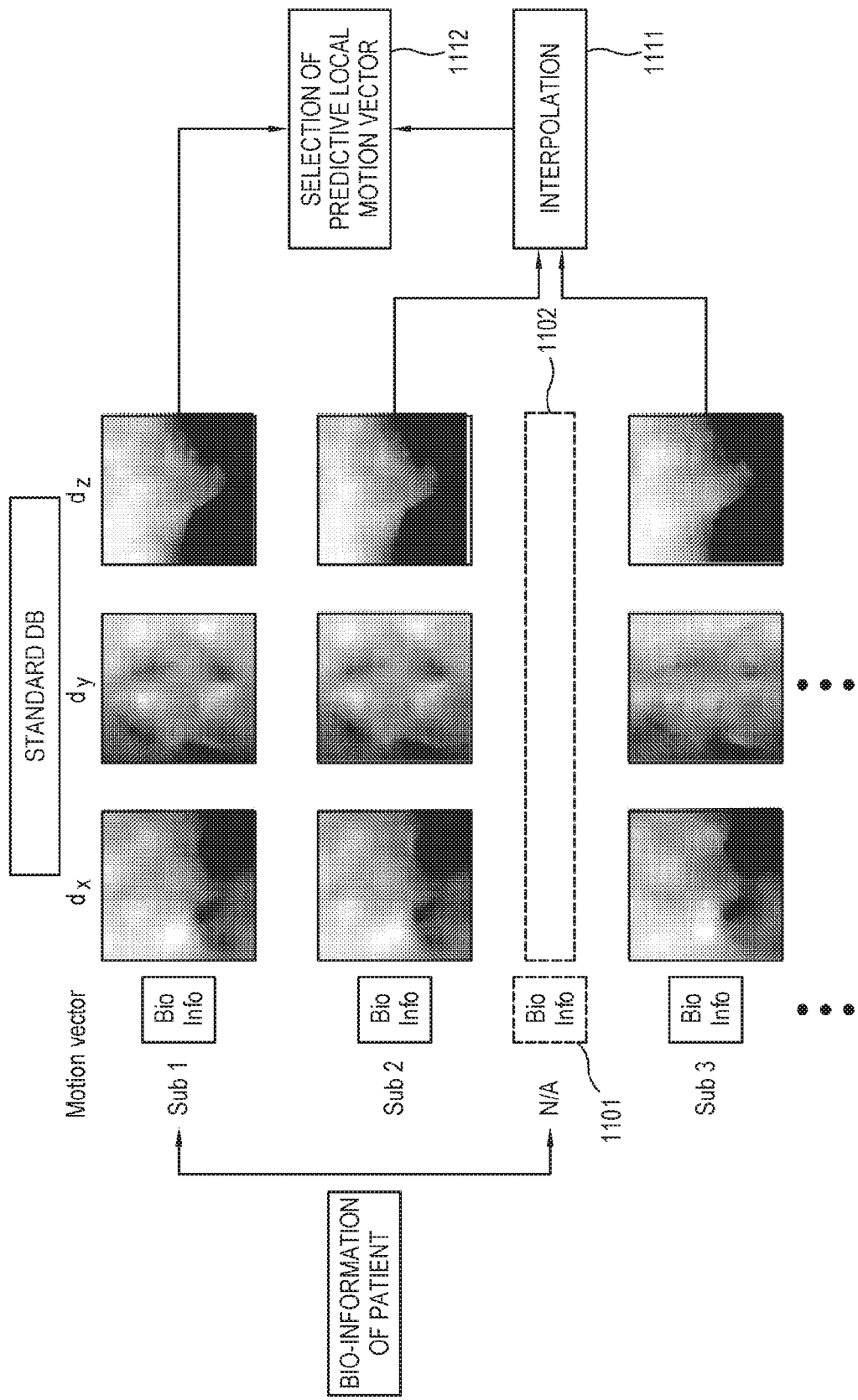

According to still another embodiment, as shown in FIG. 11, the controller 510 extracts a group, which include a predetermined number of motion vectors highly similar to the bio-information of the patient to be subjected to the diagnosis based on search from the standard DB, applies NN, linear, spline and the like interpolation to the vector data in the extracted group, and generates the predictive local motion vector 1102 corresponding to the bio-information 1101 of the patient to be subjected to the diagnosis.

Referring to FIG. 6, the controller 510 registers such a determined predictive local motion vector to the medical image (e.g. The CT image) of the patient to be subjected to the diagnosis (624). Thus, the predictive local motion vector is changed, i.e. warped corresponding to the medical image.

Figure 12:
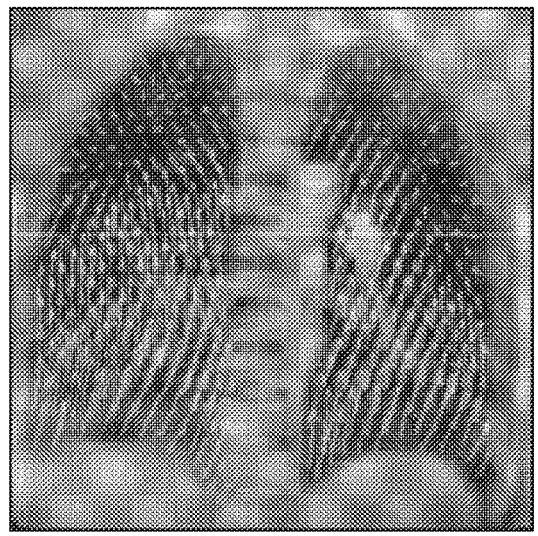

FIG. 12 illustrates an example that the predictive local motion vector determined and registered by the foregoing embodiments is displayed through the display 520.

In the image processing apparatus 100 according to the first embodiment of the present invention as shown in FIG. 6, the controller 510 uses the predictive local motion vector generated from the standard DB (i.e. the warped predictive local motion vector to normalize the local motion vector obtained by the image registration 612 between the first medical image and the second medical image according to the plurality of regions in the lungs of the anatomical entity to be subjected to the diagnosis (localized normalization) (631).

According to one embodiment, the normalization may employ a predetermined mathematical operation (subtraction, division, etc.) between the local motion vector and the predictive local motion vector. According to the present invention, there are no limits to the method of the normalization. In the first embodiment shown in FIG. 6, the normalization may be achieved by various methods so that the conditions (i.e. the information) are distinguishable according to the regions of the lungs in accordance with difference between the local motion vector and the predictive local motion vector with respect to a predetermined reference.

Further, the controller 510 performs a motion analysis according to the regions of the lung (or locally) based on the normalized local motion vector (632).

Figure 13:
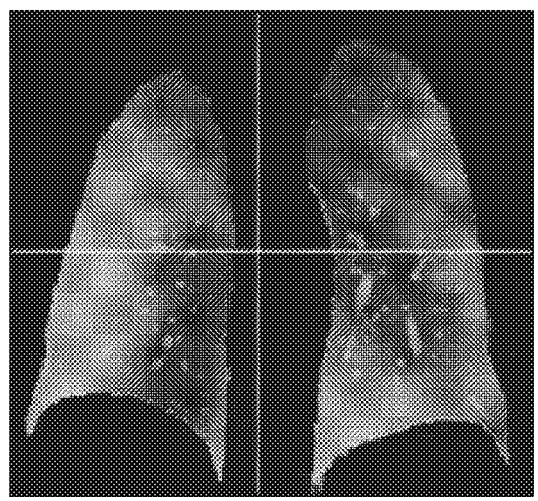

FIG. 13 illustrates an example that the medical image including the normalized local motion vector is displayed for the motion analysis through the display 520.

Here, the motion analysis includes processes of calculating major mechanical features to be used in analyzing a pulmonary disease, for example, volume change, strain, distortion, non-rigidity, etc. and selecting and extracting a highly-related feature in accordance with calculation results.

According to one embodiment of the present invention, the controller 510 of the image processing apparatus 100 calculates a factor, for example, contraction/relaxation, motion, and the like which can represent kinematic function ability normalized by combination of extracted features, and displays a medical image produced corresponding to the factor as a predetermined map (e.g. a kinematic function map) through the display 520.

Figure 14:
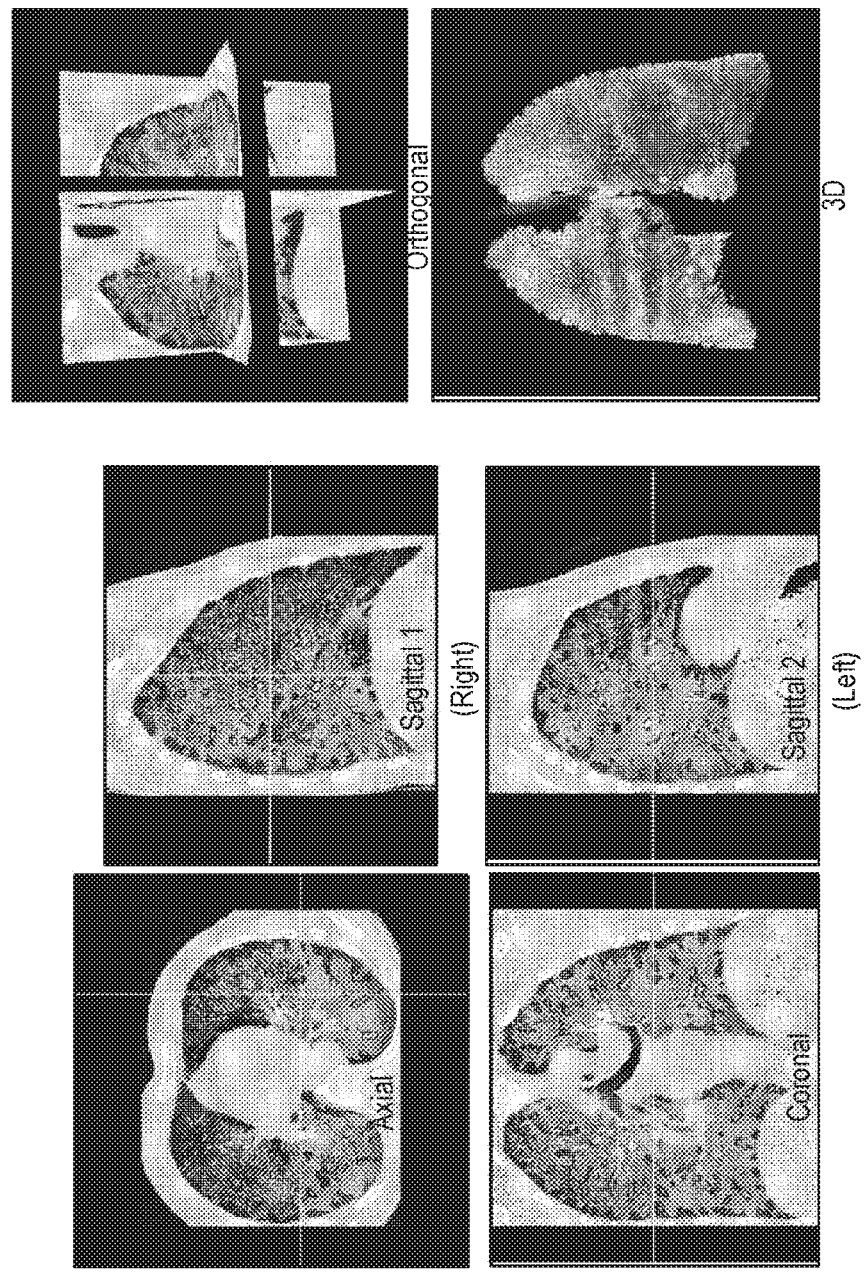

FIG. 14 illustrates an example that the medical image is displayed as the kinematic function map in accordance with the motion analysis and the feature extraction.

As shown in FIG. 14, the controller 510 may control the display 520 to display the normalized local motion vectors to be distinguishable according to the regions of the lungs (e.g. The lobes of the lungs). Here, the kinematic function map may be displayed with analysis results according to voxels on the regions of the left and right lungs, and with pieces of stochastic/statistic information (e.g. standard information such as average values of patients corresponding to certain age and certain sex) to be distinguishable according to the regions.

According to one embodiment, the kinematic function map may show the lungs (i.e. the anatomical entity) viewed in various directions (e.g. axial, orthogonal, coronal, sagittal views) as shown in FIG. 14, and may show one of the left and right lungs as necessary. Further, the anatomical entity may be displayed in the form of 3D to be rotatable and or enlargeable in a predetermined direction in response to a user's control. Therefore, a user (or a doctor) can check the conditions of the anatomical entity according to the regions, thereby more easily diagnosing the anatomical entity.

When the COPD is diagnosed, high-frequency thermotherapy, pneumectomy, etc. may be selected. To this end, there is a need of displaying the entity so that accurate diagnosis can be made according to the regions of the lungs.

Figure 15:
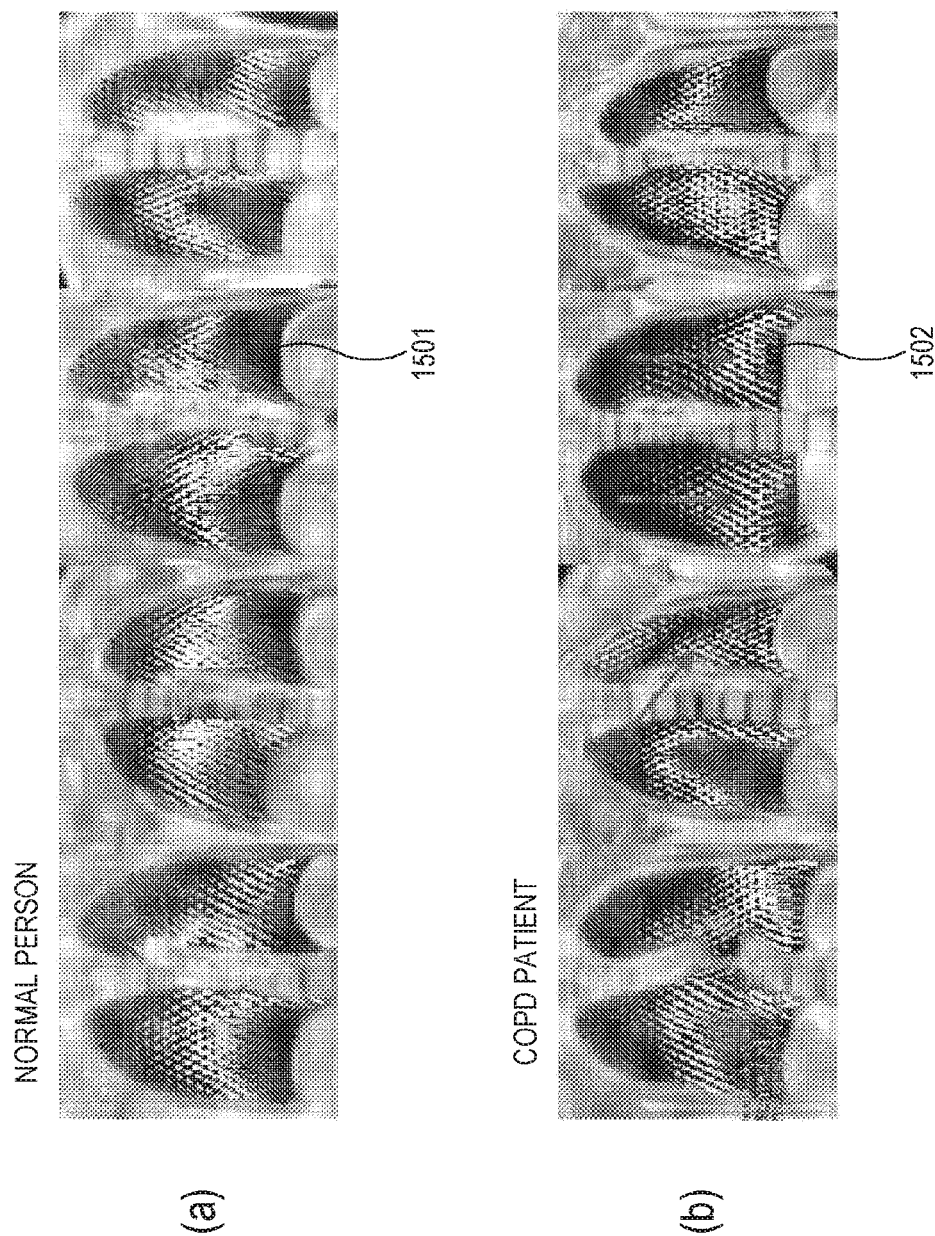
FIG. 15 illustrates comparison in motion vector between a normal person and a chronic obstructive pulmonary disease (COPD) patient according to regions.

FIG. 15 illustrates comparison in motion vector between a normal person and a COPD patient according to regions.

The normal person shows a large motion value in the lower lobe 1501 of the lung as shown in FIG. 15(a), whereas the COPD patient shows a relatively small motion value in the lower lobe 1502 of the lung as compared with that of the normal person as shown in FIG. 15(b).

Therefore, like the image processing apparatus 100 according to the first embodiment of the present invention, when the motion values according to the regions (i.e. the local motion vectors) are distinguishably displayed, it is easier to diagnose and treat the COPD.

Below, an image processing method according to the first embodiment of the present invention will be described with reference to the accompanying drawings.

Figure 16:
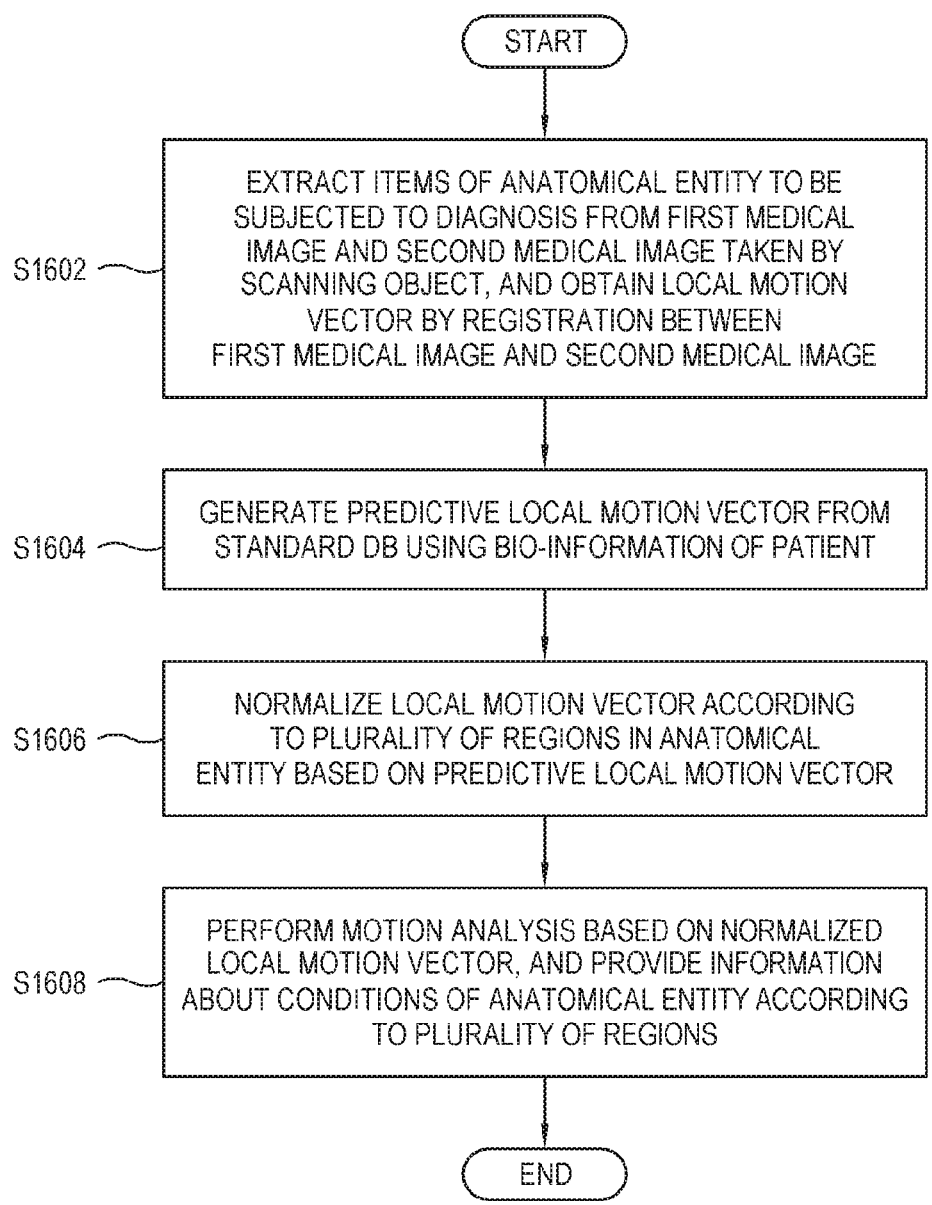
FIG. 16 is a flowchart of showing an image processing method according to the first embodiment of the present invention.

FIG. 16 is a flowchart of showing the image processing method according to the first embodiment of the present invention.

As shown in FIG. 16, the controller 510 of the image processing apparatus 100 extracts regions corresponding to the anatomical entity to be subjected to the diagnosis, i.e. the lung with regard to the first medical image and the second medical image acquired by scanning an object having the plurality of anatomical entities, and registers the first medical image and the second medical image, in which the pulmonary regions are extracted, thereby obtaining the local motion vector (S1602). Here, the medical image may for example be a thoracic CT image or a respiratory CT image including a lung, a diaphragm and a rib, in which the first medical image may correspond to the inspiratory image and the second medical image may correspond to the expiratory image. The controller 510 controls the image processor 530 to selectively segment the region corresponding to the lung through a predetermined image processing process, and controls the display 520 to display the third medical image based on the image including the local motion vector generated by region segmentation and registration. The local motion vector obtained in the step S1602 may correspond to the displacement vector derived by the image registration between the first medical image and the second medical image.

The controller 510 generates the predictive local vector from the standard DB 622 based on the bio-information of the patient to be subjected to the diagnosis (S1604). Here, the standard DB may be built by vectorizing the plurality of medical images (e.g. The respiratory CT image including the inspiratory image and the expiratory image) collected with regard to the predetermined anatomical entity, i.e. the lung, and applying predetermined statistical modeling to the vectorized data. The bio-information of the patient includes at least one among the physical information, the biological information and the habitual information. According to one embodiment the controller 510 receives the bio-information of the patient to be subjected to the diagnosis as a variable, and applies the received variable to the function corresponding to the standard DB 622, thereby finding the predictive local vector. According to another embodiment, the controller 510 may search the local motion vector corresponding to the bio-information of the patient to be subjected to the diagnosis from the standard DB 622, and find the predictive local vector in accordance with the search results. According to still another embodiment, the controller 510 may select two or more local motion vectors having the bio-information similar to that of the patient from the standard DB 622, and apply the interpolation to the two or more local motion vectors, thereby finding the predictive local motion vector.

The controller 510 uses the predictive local motion vector generated in the step 1604 to normalize the local motion vector obtained in the step 1602 according to the plurality of regions in the anatomical entity, i.e. the lung (S1606). Here, the plurality of regions in the lung are lobes of the lungs, in which the right lung includes three regions of an upper lobe, a middle lobe and a lower lobe, and the left lung includes two regions of an upper lobe and a lower lobe. The controller 510 registers the predictive local motion vector generated in the step 1604 to the third medical image generated by the registration in the step S1602, and applies the warped predictive local vector to the third medical image in accordance with the registration, thereby normalizing the local motion vector obtained in the step 1602 according to the plurality of regions. The normalization refers to displaying conditions of the lungs to be distinguishable according to the plurality of regions based on difference between the local motion vector and the predictive local motion vector with respect to a predetermined reference. According to one embodiment, the normalization may use a predetermined mathematical operation such as subtraction and division.

Further, the controller 510 performs the motion analysis according to the plurality of regions based on the local motion vector normalized in the step S1606, and provides information about the conditions of the anatomical entity to be subjected to the diagnosis based on the analysis results according to the plurality of regions subjected to the motion analysis (S1608). Here, the controller 510 may calculate at least one factor that can represent the kinematic function ability normalized according to the results of the motion analysis, and control the display 520 to display the medical image generated corresponding to the factor as a fourth medical image in the form of a map of a predetermined method. The fourth medical image may be displayed to show the analysis results distinguishably according to voxels on the regions of the left and right lungs (i.e. the lobes of the lungs), and further show the standard information of the patient to be subjected to the diagnosis according to the regions, thereby making it easy to recognize difference between the pulmonary-disease patient and a normal person. Thus, a user can diagnose a predetermined anatomical entity, i.e. a lung based on the information about the conditions according to the regions.

As above, the controller 510 of the image processing apparatus 100 according to the first embodiment of the present invention normalizes the local motion vector obtained by the registration between the inspiratory image and the expiratory image through the predictive local motion vector generated from the standard DB, and provides information about the conditions of the lung based on the normalized local motion vector according to the plurality of regions.

By the normalization according to the regions, it is possible to provide distinguishable information about difference between the local motion vector of the pulmonary disease patient to be subjected to the diagnosis and a predictive local motion vector of a normal person generated from the standard DB through the statistical modeling using the bio-information of the patient, and a doctor and the like user can use the information in diagnosing the pulmonary disease.

Therefore, a user can more accurately and segmentally make a diagnosis since severity indicating the seriousness of the COPD and the like pulmonary disease can be quantized and displayed according to the regions of the lung based on difference in the kinematic function of the lung from a normal person.

Next, a second embodiment of the present invention will be described.

The controller 510 of the image processing apparatus 100 according to the second embodiment of the present invention extracts regions corresponding to a predetermined anatomical entity to be subjected to a diagnosis from the first medical image and the second medical image acquired by scanning an object having the plurality of anatomical entities, and produces a third medical image by registration between the first medical image and the second medical image from which the regions are extracted. Therefore, the second embodiment is similar to the first embodiment in using the image registration.

According to the second embodiment, the controller 510 computes a density parameter from the registered medical image, and further computes a texture parameter. In addition, the controller 510 computes a kinematic function parameter based on the computed parameters. Here, the computed kinematic function parameter may include a factor, for example, contraction/relaxation, motion, and the like which can represent the kinematic function ability like that of the first embodiment.

According to the second embodiment, the controller 510 classifies the medical images through repetitive training with regard to the computed kinematic function parameter, and makes the COPD severity be graded according to the classification (COPD severity grading). Here, the controller 510 may further selectively perform supervised learning as necessary in the training process.

According to one embodiment, the COPD severity grading may be for example achieved by stepwise classifying the seriousness of the COPD into mild, moderate, severe, etc. The steps may be determined by taking pain, curability, etc. into account.

Further, the controller 510 controls the display 520 to display the COPD severity grading results, in which the COPD grade may be displayed as overlaid on CT statistical text information (statistical text info), and the statistical text information may be extracted from the standard DB of the first embodiment.

Below, an image processing method according to the second embodiment of the present invention will be described with reference to the accompanying drawings.

Figure 17:
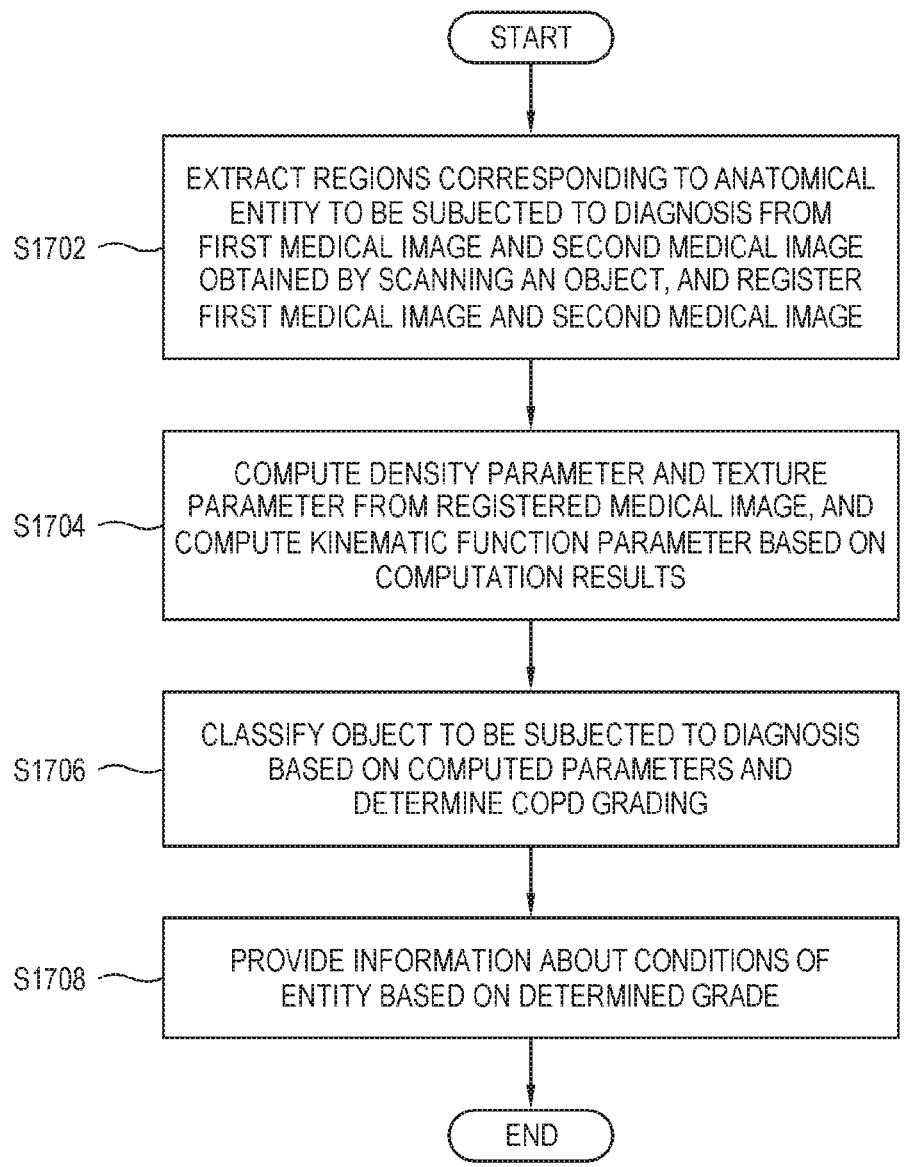
FIG. 17 is a flowchart of showing an image processing method according to a second embodiment of the present invention.

FIG. 17 is a flowchart of showing the image processing method according to a second embodiment of the present invention.

As shown in FIG. 17, the controller 510 of the image processing apparatus 100 according to the second embodiment extracts regions corresponding to the anatomical entity to be subjected to the diagnosis, i.e. the lung from the first medical image and the second medical image obtained by scanning an object including the plurality of anatomical entities, and obtains the local motion vector by registration between the first medical image and the second medical image from which the pulmonary regions are extracted (S1702).

The controller 510 computes a density parameter and a texture parameter from the medical image registered in the step S1702, and further computes a kinematic function parameter based on computation results (S1704).

The controller 510 classifies the anatomical entity to be subjected to the diagnosis based on the parameters computed in the step S1704, and determines the COPD grading (S1706).

Further, the controller 510 may provide a degree of COPD seriousness or the like as the information about the conditions of the anatomical entity to be subjected to the diagnosis, i.e. the lungs, based on the grade determined in the step S1706, through the display 520 (S1708).

As above, the controller 510 of the image processing apparatus 100 according to the second embodiment of the present invention computes a kinematic function parameter based on density and texture information of the medical image obtained by registration between the inspiratory image and the expiratory image, and determines the pulmonary disease, specifically, the COPD grade based on the computed parameters, thereby providing the corresponding information. Therefore, a user can more accurately and segmentally diagnose the pulmonary disease according to degrees of COPD seriousness.

Next, a third embodiment of the present invention will be described.

The controller 510 of the image processing apparatus 100 according to the third embodiment of the present invention makes a medical image obtained by scanning an object including an anatomical entity to be subjected to a diagnosis be reconfigured based on lesion quantized information, and displays the reconfigured medical image at a predetermined reading viewpoint. Therefore, the third embodiment is similar to the first and second embodiments in that the medical image is processed to be convenient in the diagnosis.

The foregoing medical image reconfigured according to the third embodiment may be an integrated 3D readout image. The controller 510 may use the pulmonary disease quantization information to reconfigure a diagnosis image.

Specifically, the controller 510 may normalize quantization information of a lesion in accordance with clinical severity to be visualized on the display 520. Here, the quantization refers to digitization of values corresponding to various factors used in diagnosing the pulmonary disease so as to be displayed on one integrated medical image.

According to the third embodiment of the present invention, the integrated 3D readout image is generated to diagnose various pulmonary diseases such as nodule, airway, blood vessel, and pulmonary emphysema. Here, the controller 510 computes a transformation function (e.g. a transfer function or a multi-dimension transfer function) to which clinical importance of each pulmonary disease is reflected, and uses the computed transfer function to generate the integrated 3D readout image. According to one embodiment, the transformation function may employ the standard DB and the like statistical modeling as described in the first embodiment.

In such a manner, the controller 510 measures information about various diseases when a CT image of a patient is input, and applies the transformation function to each disease, thereby transforming the input CT image into the integrated 3D readout image.

The controller 510 may reconfigure the integrated 3D readout image at an optimal viewpoint where the lesions are not overlapped. For example, when the lesions are dense, the controller 510 computes a viewpoint at which the lesions are dispersed as far apart as possible, and thus provides a view suitable for reading out each individual lesion based on the computation results. Here, the controller 510 may make change the integrated readout image by rotation, distortion, etc. and may control the image processor 530 to variously reconfigure the image by enlarging some regions, adjusting the size, changing a flat image into a curved image, etc.

The image processing apparatus 100 according to the third embodiment of the present invention may provide a selective analysis tool for selecting a region corresponding to a specific pulmonary disease in the integrated readout image. For example, the controller 510 may control the display 520 to selectively display only the airway in the integrated readout image in response to a user's selection.

Below, an image processing method according to the third embodiment of the present invention will be described with reference to the accompanying drawings.

Figure 18:
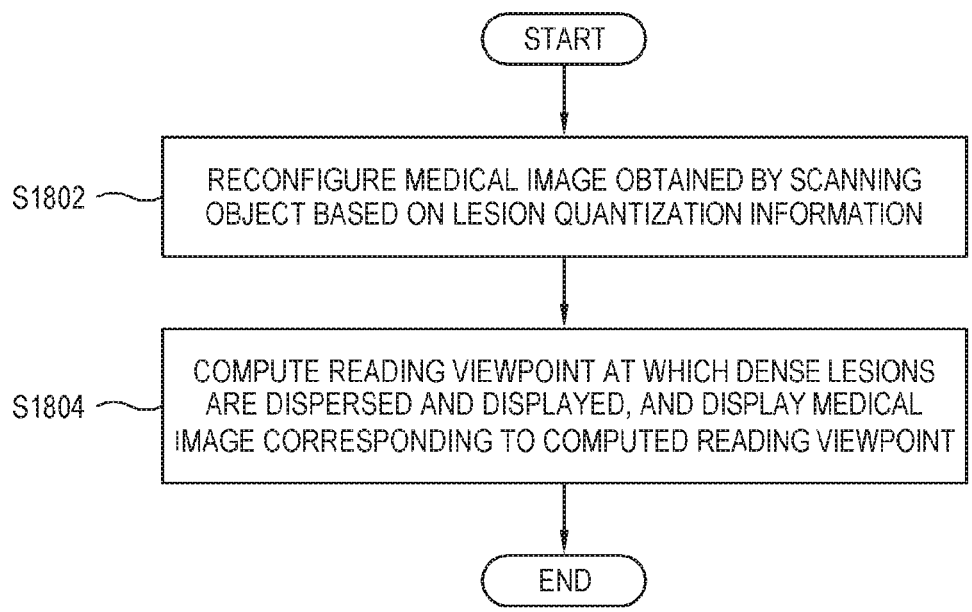
FIG. 18 is a flowchart of showing an image processing method according to a third embodiment of the present invention.

FIG. 18 is a flowchart of showing an image processing method according to the third embodiment of the present invention.

As shown in FIG. 18, the controller 510 of the image processing apparatus 100 according to the third embodiment reconfigures the medical image (e.g. the respiratory CT image) obtained by scanning an object, i.e. a chest based on the lesion quantization information (S1802).

The controller 510 computes a reading viewpoint at which the dense lesions are dispersed and displayed on the medical image reconfigured in the step S1802, and displays the medical image corresponding to the computed reading viewpoint (S1804).

FIGS. 19 to 25 are views of showing various examples that an image processing apparatus according to the third embodiment of the present invention provides a readout image integrated by the controller 510 and analyzes a lesion based on the readout image.

Figure 19:
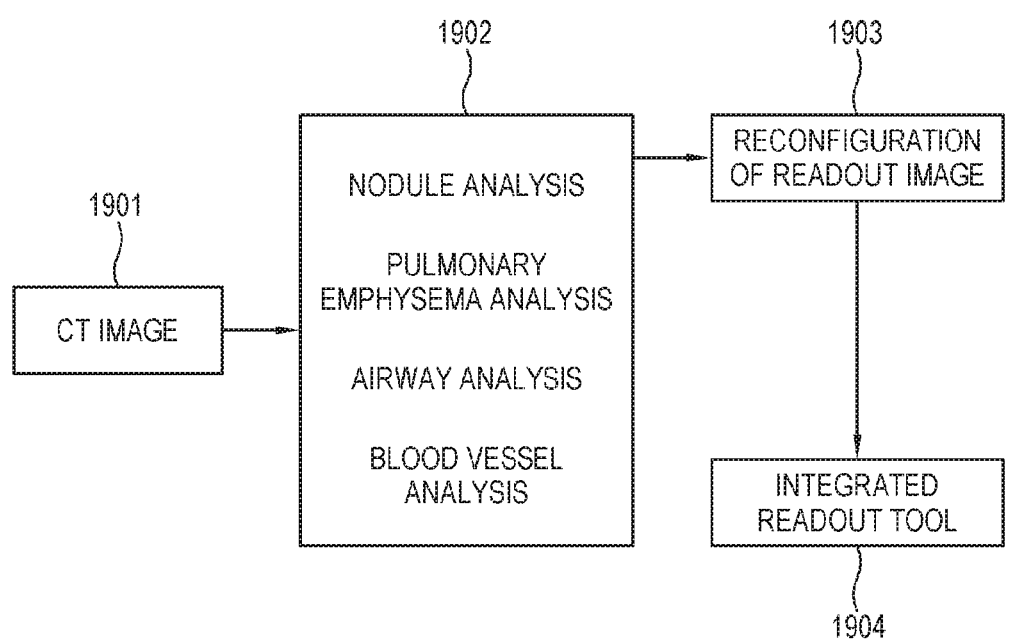
FIGS. 19 to 25 are views of showing various examples that an image processing apparatus according to the third embodiment of the present invention provides a readout image integrated by a controller and analyzes a lesion based on the readout image.

As shown in FIG. 19, the image processing apparatus 100 receives a CT image of a patient (1901), and the controller 510 analyzes a plurality of lesions from the received CT image (1902). Here, the received CT image may be a currently taken medical image or a previously taken medical image. That is, when the image processing apparatus 100 is the medical apparatus (for example, the CT apparatus of FIG. 2 and FIG. 3), the CT image, of which data obtained by scanning an object is processed by the image processor 266, may be received. Further, when the image processing apparatus 100 is a display apparatus including a portable apparatus, the CT image may be received from an external medical apparatus through data communication.

According to the third embodiment, the image processing apparatus 100 receives at least one CT image obtained by scanning a predetermined patient. That is, the third embodiment includes a case that the image processing apparatus 100 receives a plurality of CT images, and the plurality of CT images may be aggregation of data obtained at various scanning angles.

The controller 510 may analyze various lesions of the anatomical entity, i.e. the lung included in the received CT image, and may specifically perform a nodule analysis, a pulmonary emphysema analysis, an airway analysis and a blood vessel analysis as shown in FIG. 19 (1902).

Further, the controller 510 may reconfigure the medical image (or the tomography image) obtained by scanning the object into an integrated 3D readout image based on the lesion analysis results (1903).

The reconfigured integrated readout image is displayed on the display 520 through an integrated readout tool provided by the image processing apparatus 100 (1904). The integrated readout tool provides an optimal view suitable for reading out each lesion in the integrated readout image, and thus a user can check conditions of each individual lesion.

Figure 20:
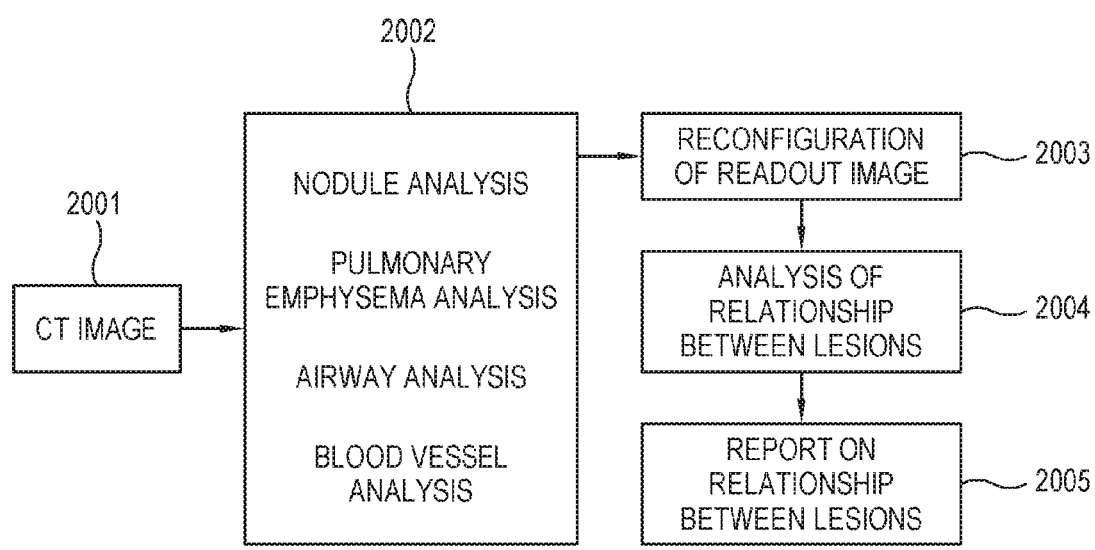

Like the embodiment shown in FIG. 19, the image processing apparatus 100 in the embodiment shown in FIG. 20 receives a CT image (or a plurality of medical images) of a patient (2001), and the controller 510 performs an analysis with regard to a plurality of lesions from the received CT image (2002). Here, the controller 510 may analyze various lesions of the anatomical entity, i.e. the lung included in the received CT image, and may specifically perform a nodule analysis, a pulmonary emphysema analysis, an airway analysis and a blood vessel analysis as shown in FIG. 20 (2002).

The controller 510 reconfigures the medical image (or the tomography image) obtained by scanning the object into an integrated 3D readout image based on the lesion analysis results (2003).

The controller 510 analyzes a relationship between the lesions based on the reconfigured integrated readout image (2004).

Further, the controller 510 generates a lesion-relation report in accordance with the analysis results, and displays it through the display 520 (2005). Here, the generated report may be transmitted to the outside in the form of a predetermined file, or printed through a printing apparatus connected to the image processing apparatus 100.

A user checks a relationship between the lesions based on the lesion-relationship report, and utilizes it in the diagnosis.

Figure 21:
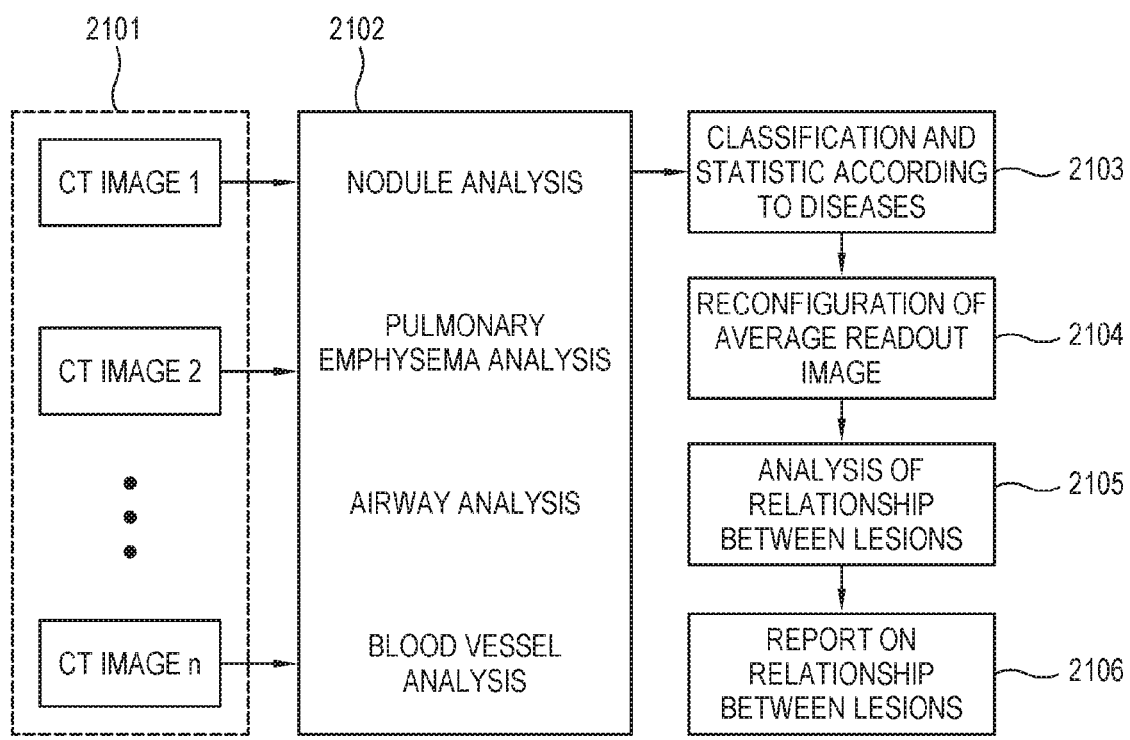

In the embodiment shown in FIG. 21, the image processing apparatus 100 receives a plurality of CT images corresponding to a plurality of patients (2101). Here, the plurality of CT images may be the medical images taken with regard to patients who belong to a predetermined user group having certain age or certain sex.

The controller 510 analyzes the plurality of lesions with regard to the plurality of received CT images (2102). Here, the controller 510 analyze various lesions of the anatomical entity to be subjected to the diagnosis, i.e. the lung according to the received CT images, and may specifically perform a nodule analysis, a pulmonary emphysema analysis, an airway analysis and a blood vessel analysis as shown in FIG. 21 (2102).

The controller 510 makes the results of lesion analysis performed with regard to the CT images be classified according to diseases, and compiles statistics thereof (2103).

The controller 510 may reconfigure an average readout image corresponding to the classification and statistic results (2104).

Further, the controller 510 analyzes a relationship between the lesions based on the reconfigured average readout image (2105), and makes a report on the relationship between the lesions according to analysis results, thereby displaying the report through the display 520 (2106). Here, the report may be transmitted to the outside in the form of a predetermined file, or printed through a printing apparatus connected to the image processing apparatus 100.

Therefore, a user can check an average relationship between the lesions in a certain patent group through the report on the relationship between the lesions, and use it in the diagnosis.

Figure 22:
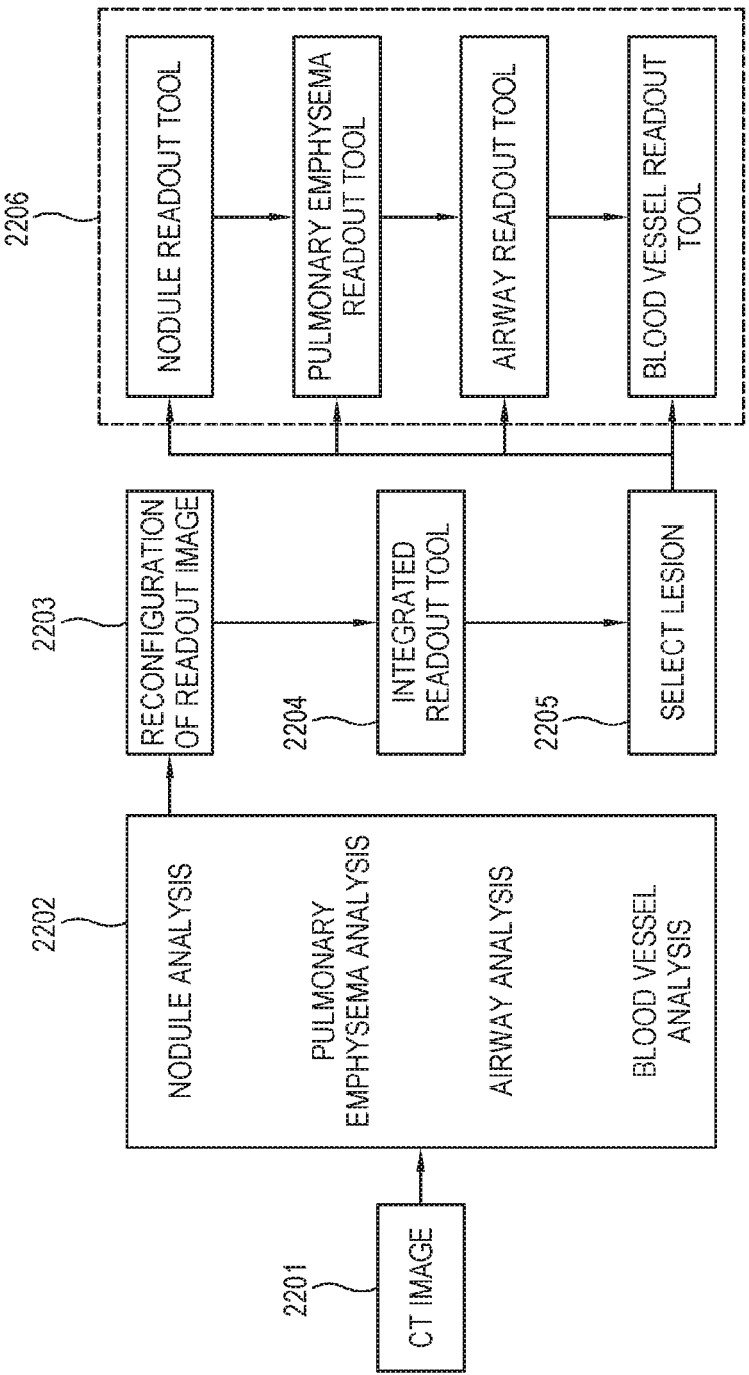

Like the embodiment shown in FIG. 19, the image processing apparatus 100 in the embodiment shown in FIG. 22 receives a CT image (or a plurality of medical images) of a patient (2201), and the controller 510 performs an analysis with regard to a plurality of lesions from the received CT image (2202). Here, the controller 510 may analyze various lesions of the anatomical entity, i.e. the lung included in the received CT image, and may specifically perform a nodule analysis, a pulmonary emphysema analysis, an airway analysis and a blood vessel analysis as shown in FIG. 22 (2202).

The controller 510 reconfigures the medical image (or the tomography image) obtained by scanning the object into an integrated 3D readout image based on the lesion analysis results (2203).

The reconfigured integrated readout image is displayed on the display 520 through an integrated readout tool provided by the image processing apparatus 100 (2204). The integrated readout tool provides an optimal view suitable for reading out each lesion in the integrated readout image, and thus a user can check conditions of each individual lesion.

The integrated readout tool may be provided to allow a user to select a lesion. A user can select a specific lesion through the user input receiver 540 (2205), and the controller 510 controls the display 520 to display an image, through which conditions of a specific lesion (e.g. nodule, pulmonary emphysema, etc.) are checkable, through the readout tool for the corresponding lesion in response to a user's selection (2206).

A user can check conditions of a predetermined selected lesion, and utilizes it in the diagnosis.

Figure 23:
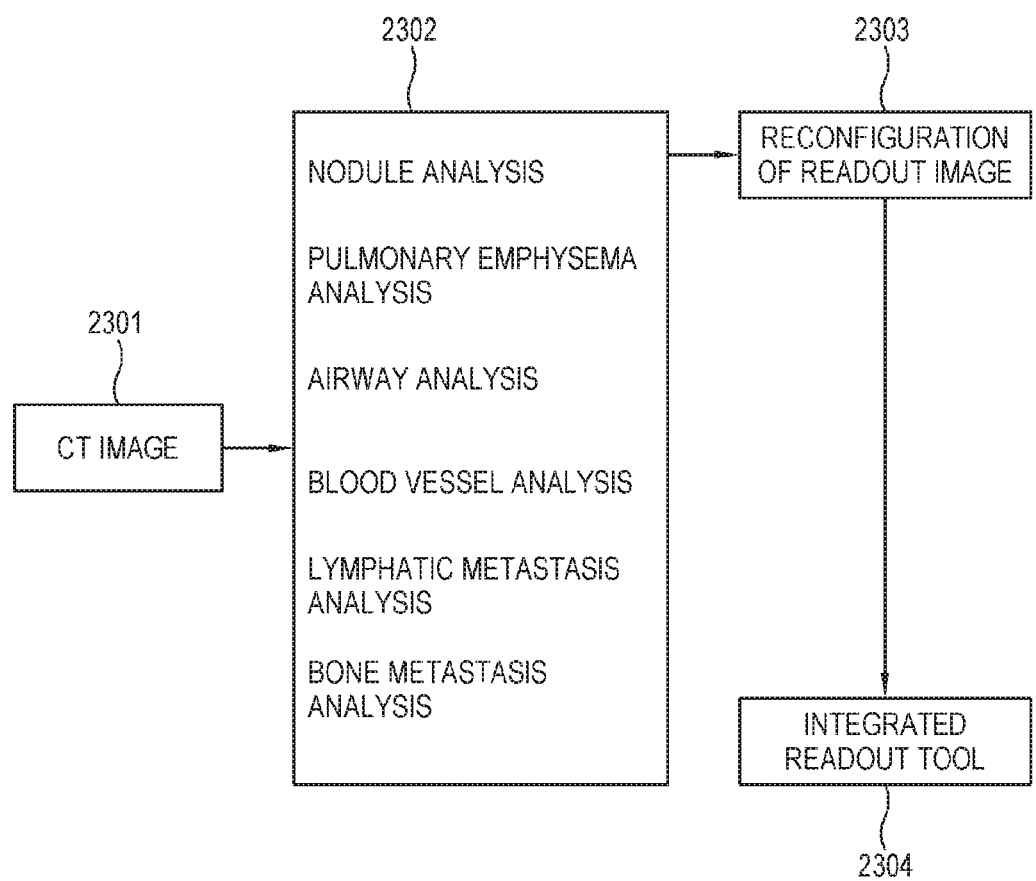

Like the embodiment shown in FIG. 19, the image processing apparatus 100 in the embodiment shown in FIG. 23 receives a CT image (or a plurality of medical images) of a patient (2301), and the controller 510 performs an analysis with regard to a plurality of lesions from the received CT image (2302). Here, the controller 510 may analyze various lesions of the anatomical entity, i.e. the lung included in the received CT image, and may specifically perform a lymphatic metastasis analysis and a bone metastasis analysis as well as a nodule analysis, a pulmonary emphysema analysis, an airway analysis and a blood vessel analysis as shown in FIG. 23 (2302).

The controller 510 reconfigures the medical image (or the tomography image) obtained by scanning the object into an integrated 3D readout image based on the lesion analysis results (2303).

The reconfigured integrated readout image is displayed on the display 520 through an integrated readout tool provided by the image processing apparatus 100 (2304). The integrated readout tool provides an optimal view suitable for reading out each lesion in the integrated readout image, and thus a user can check conditions of each individual lesion.

In the embodiment of FIG. 23, a user may use the integrated readout tool to check not only the conditions of each individual lesion in the lung but also lymphatic or bone metastasis, and thus utilizes it in the diagnosis.

Figure 24:
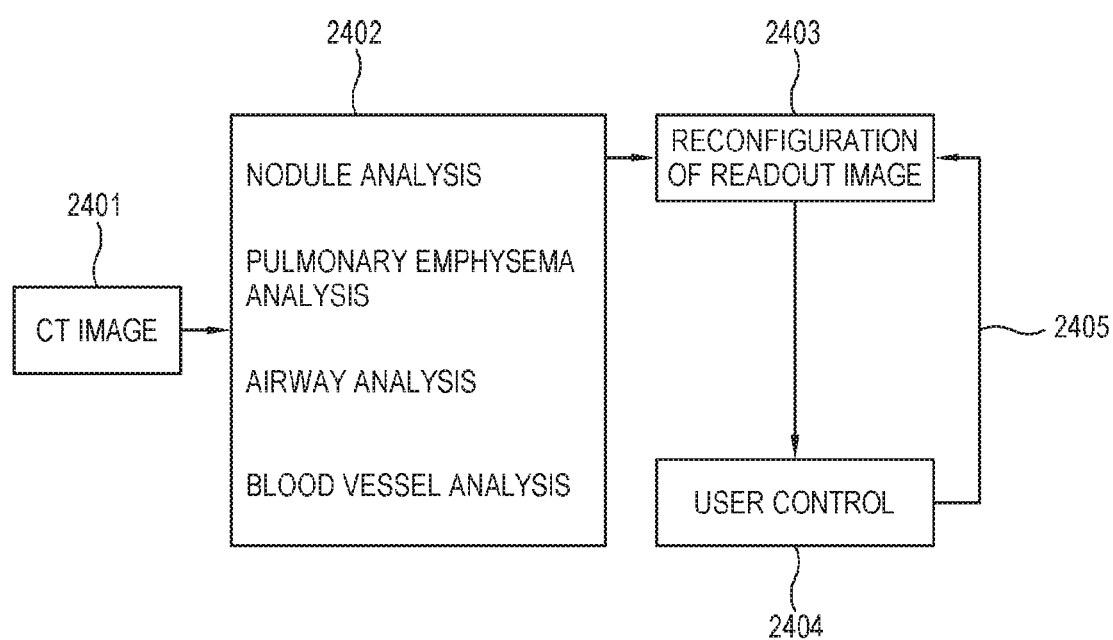

Like the embodiment shown in FIG. 19, the image processing apparatus 100 in the embodiment shown in FIG. 24 receives a CT image (or a plurality of medical images) of a patient (2401), and the controller 510 performs an analysis with regard to a plurality of lesions from the received CT image (2402). Here, the controller 510 may analyze various lesions of the anatomical entity, i.e. the lung included in the received CT image, and may specifically perform a nodule analysis, a pulmonary emphysema analysis, an airway analysis and a blood vessel analysis as shown in FIG. 24 (2402).

The controller 510 reconfigures the medical image (or the tomography image) obtained by scanning the object into an integrated 3D readout image based on the lesion analysis results (2403).

Here, the image processing apparatus 100 may receive a user control value with regard to the integrated CT readout image reconfigured through the user input receiver 540 (2404). The controller 510 reconfigures the readout image again in response to a user control input (2005). Further, the controller 510 may display the reconfigured readout image through the display 520.

The image processing apparatus 100 in the embodiment shown in FIG. 24 updates and displays the readout image in response to user control so as to provide information needed for a user, and utilize it in the diagnosis.

Figure 25:
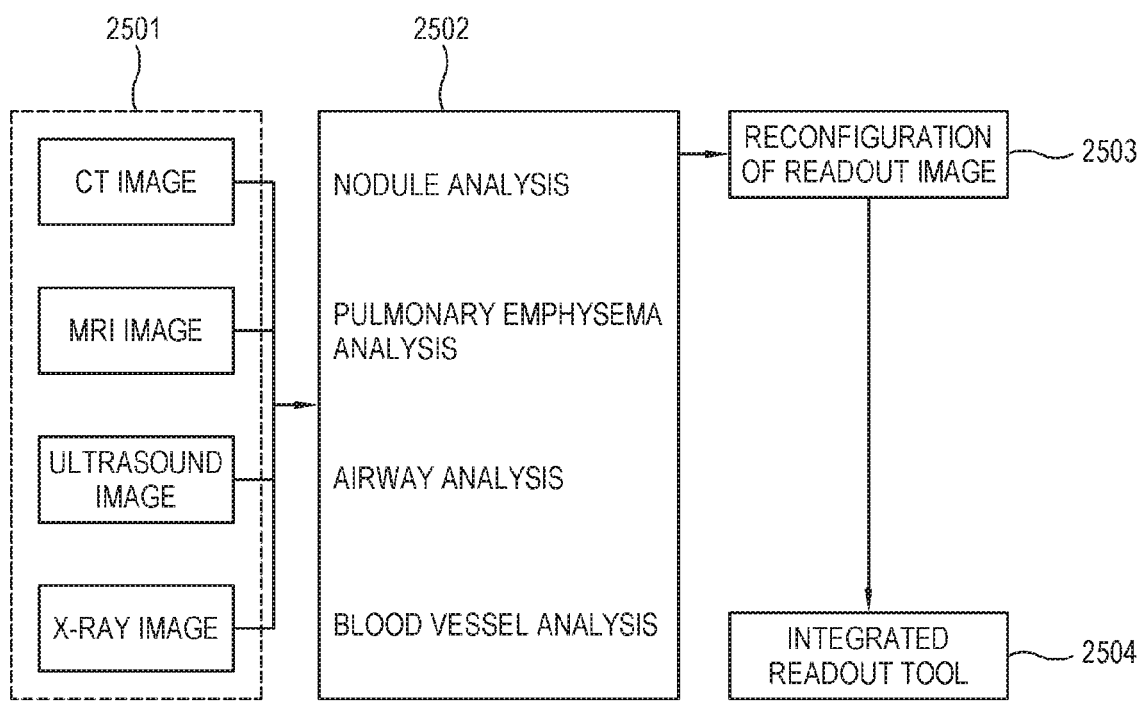

In the embodiment shown in FIG. 25, the image processing apparatus 100 may further receive a medical image obtained by other medical apparatuses in addition to a CT image of a patient (2501). Specifically, referring to FIG. 25, at least one among an MRI image, an ultrasound image and an X-ray image may be further received.

The controller 510 performs analyses with regard to a plurality of lesions from the received images (2502). Here, the controller 510 may analyze various lesions of the anatomical entity, i.e. the lung included in the received medical images, and may specifically perform a nodule analysis, a pulmonary emphysema analysis, an airway analysis and a blood vessel analysis as shown in FIG. 25 (2502).

The controller 510 reconfigures the medical image obtained by scanning an object into an integrated 3D readout image based on the results of performed lesion analyses (2503).

The reconfigured integrated readout image is displayed on the display 520 through an integrated readout tool provided by the image processing apparatus 100 (2504). The integrated readout tool provides an optimal view suitable for reading out each lesion in the integrated readout image, and thus a user can check conditions of each individual lesion.

The image processing apparatus 100 in the embodiment shown in FIG. 24 updates and displays the readout image in response to user control so as to provide information needed for a user, and utilize it in the diagnosis.

The image processing apparatus 100 in the embodiment shown in FIG. 25 may reconfigure the readout image with reference to another medical image when the CT image is difficult to check an image of a position/configuration, and thus has an advantage of providing more detailed diagnosis results.

Figure 27:
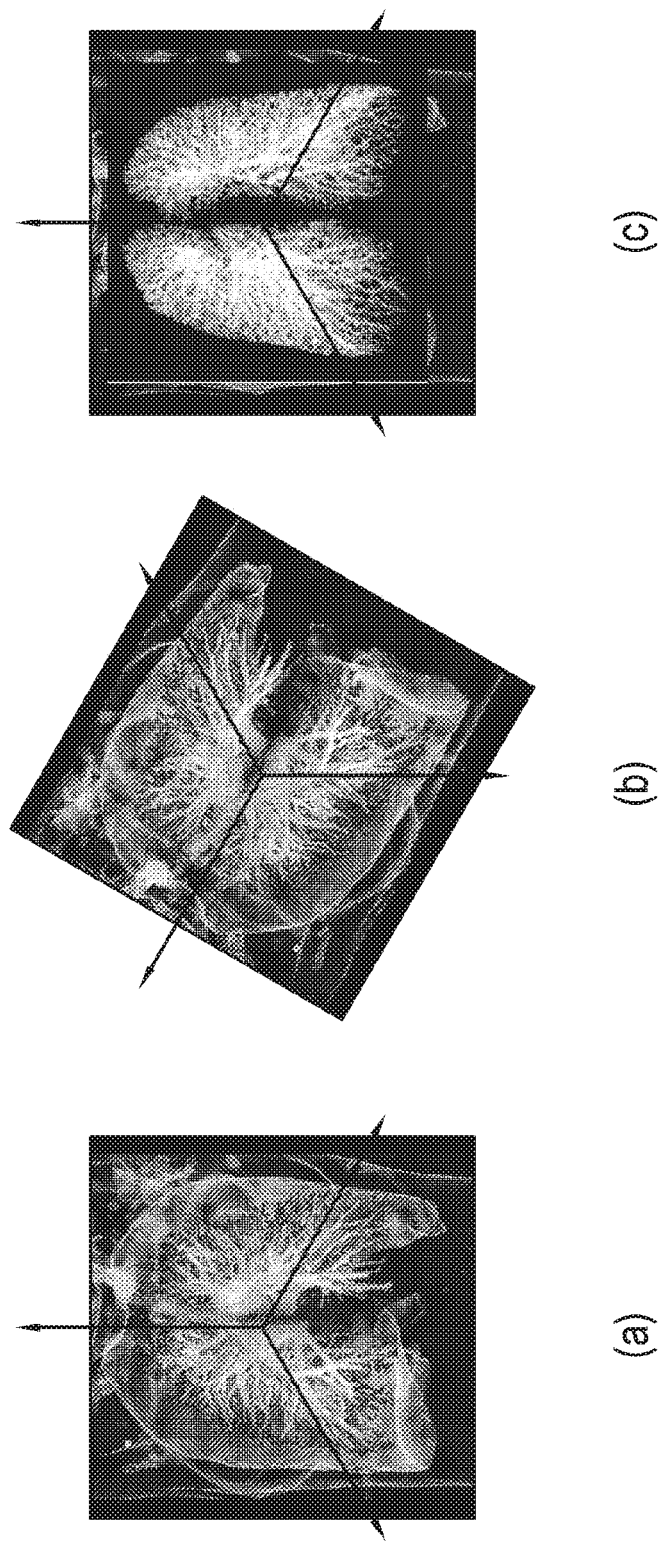

FIGS. 26 and 27 are views of showing examples that the image processing apparatus 100 according to the third embodiment of the present invention displays a reconfigured integrated CT readout image.

As shown in FIG. 26, an integrated CT readout image 2610 is a 3D image provided for checking conditions of various lesions. The integrated CT readout image may be reconfigured in various methods according to the embodiments described with reference to FIGS. 19 to 25, and provides the most suitable view for reading out each individual lesion through the integrated readout tool by computing a viewpoint at which the lesions are dispersed as far apart as possible.

The image processing apparatus 100 may adjust/change the integrated CT readout image to be displayed in response to a user's selection, and an interface 2620 for a user's input may be for example provided through the display 520 in the form of 2D coordinates as shown in FIG. 26.

The controller 510 may update the integrated CT readout image to be displayed as shown in FIG. 27 corresponding to points 2621, 2622 and 2623 selected by a user on the interface 2620. That is, the integrated image in FIG. 27(a) may be rotated toward a direction in which a specific lesion is easy to read as shown in FIG. 27(b), and may show only a specific region conspicuously in the anatomical entity, i.e. the lung as shown in FIG. 27(c). Although FIG. 27 illustrates only some among various embodiments of the integrated CT readout image, the integrated CT readout image of the third embodiment of the present invention may be displayed in various ways for diagnosing and curing diseases caused by various factors such as the kind and position of lesion, a diagnosing purpose, a history of a patient, etc.

The image processing apparatus 100 according to the third embodiment of the present invention has an advantage of analyzing and diagnosing various pulmonary diseases through the integrated diagnosis image, as compared with the conventional art where the CT image provides an analysis for only a single pulmonary disease.

According to the foregoing embodiments of the present invention, the image processing apparatus 100 displays a medical image in various ways by providing normalization according to regions, classification and grading using a kinematic function parameter, an integrated readout image, or the like with regard to a medical image including a predetermined anatomical entity, so that a doctor and the like user can make good use of the medical image in diagnosing a pulmonary disease.

Features according to many embodiments of the present invention may be partially or entirely united or combined to each other, and technically variously interlocked and driven as fully understood by a person having an ordinary skill in the art, and the embodiments may be realized independently of or together with each other.

Meanwhile, the foregoing exemplary embodiments of the present invention may be realized by a computer readable recording medium. The recording medium includes a storage medium for storing a program readable by a computer system. The program may be transmitted and received through a transmission medium materialized by a wired/wireless network where computer systems are linked.

The foregoing exemplary embodiments may be realized by hardware and combination between hardware and software. As the hardware, the controller 510 may include a nonvolatile memory in which a computer program is stored as the software, a RAM in which the computer program stored in the nonvolatile memory is loaded, and a CPU for executing the computer program loaded in the RAM. The nonvolatile memory may include a hard disk drive, a flash memory, a ROM, CD-ROMs, magnetic tapes, a floppy disc, an optical storage, etc., but is not limited thereto. The nonvolatile memory is a kind of computer-readable recording medium in which a program readable by a computer of the present invention is recorded.

The computer program is a code that is read and executed by the CPU, and includes codes for performing the operations of the controller 510 such as the operations S1601 to S1608, S1702 to S1708, and S1802 to S1804 as shown in FIGS. 16 to 18.

The computer program may be included in an operating system provided in the image processing apparatus 100 or software including an application and/or software interfacing with an external apparatus.

Although the present invention has been shown and described through exemplary embodiments, the present invention is not limited to the exemplary embodiments and may be variously materialized within the appended claims.

REFERENCE NUMERALS

100: image processing apparatus
510: controller
520: display
530: image processor
540: user input receiver
550: storage
560: communicator

The invention claimed is:

1. An image processing apparatus comprising:
a storage configured to comprise a standard database (DB) established based on information about a predetermined anatomical entity; and
at least one processor configured to:
obtain a local motion vector by registration between a first medical image and a second medical image taken by scanning an object including the anatomical entity,
obtain a predictive local motion vector from the standard database (DB) corresponding to an information of a patient to be subjected to a diagnosis,
normalize the local motion vector according to a plurality of regions in the anatomical entity based on difference between the local motion vector and the predictive local motion vector to perform a motion analysis according to the plurality of regions in the anatomical entity based on the normalized local motion vector, and
provide information about conditions of the anatomical entity based on the normalized local motion vector according to the plurality of regions.

2. The image processing apparatus according to claim 1, further comprising:
a display configured to display the information about the conditions of the anatomical entity distinguishable according to the plurality of regions.

3. The image processing apparatus according to claim 1, wherein the at least one processor is further configured to:
extract a region corresponding to the anatomical entity from the first medical image and the second medical image, and
obtain the local motion vector corresponding to a displacement vector derived based on the registration between the first medical image and the second medical image from which the region corresponding to the anatomical entity is extracted.

4. The image processing apparatus according to claim 3, wherein the anatomical entity comprises a lung, and
wherein the first medical image corresponds to an inspiratory image and the second medical image corresponds to an expiratory image.

5. The image processing apparatus according to claim 1, wherein the establishing of the standard DB comprises:
vectorizing a plurality of medical images collected with regard to the anatomical entity, and
applying statistical modeling to the vectorized plurality of medical images.

6. The image processing apparatus according to claim 5, wherein the at least one processor is further configured to:
receive bio-information about the patient to be subjected to the diagnosis as a variable, and
compute the predictive local motion vector by applying the received variable to a function corresponding to the standard DB.

7. The image processing apparatus according to claim 5, wherein the established standard DB further comprises local motion vector information corresponding to the plurality of medical images, and
wherein the at least one processor is further configured to:
search the local motion vector corresponding to bio-information about the patient to be subjected to the diagnosis from the standard DB, and
determine the predictive local motion vector based on results of the search.

8. The image processing apparatus according to claim 7, wherein the at least one processor is further configured to:
select two or more local motion vectors having similar bio-information to the patient to be subjected to the diagnosis, and
compute the predictive local motion vector by applying interpolation to the selected two or more local motion vectors.

9. The image processing apparatus according claim 1, wherein the at least one processor is further configured to:
register the predictive local motion vector generated from the standard DB to a third medical image generated by registration between the first medical image and the second medical image, and
use the predictive local motion vector warped to the third medical image by the registration to normalize the local motion vector according to the plurality of regions.

10. An image processing method comprising:
obtaining a local motion vector by registration between a first medical image and a second medical image taken by scanning an object including a predetermined anatomical entity;
obtaining a predictive local motion vector from a standard database (DB) corresponding to an information of a patient to be subjected to a diagnosis;
normalizing the local motion vector according to a plurality of regions in the anatomical entity based on difference between the local motion vector and the predictive local motion vector to perform a motion analysis according to the plurality of regions in the anatomical entity based on the normalized local motion vector; and
providing information about conditions of the anatomical entity based on the normalized local motion vector according to the plurality of regions.

11. The image processing method according to claim 10, wherein the obtaining of the local motion vector comprises:
extracting a region corresponding to the anatomical entity from the first medical image and the second medical image, and
obtaining the local motion vector corresponding to a displacement vector derived by the registration between the first medical image and the second medical image from which the region of the anatomical entity is extracted,
wherein the anatomical entity comprises a lung, and
wherein the first medical image corresponds to an inspiratory image and the second medical image corresponds to an expiratory image.

12. The image processing method according to claim 10, further comprising:
vectorizing a plurality of medical images collected with regard to the anatomical entity; and
establishing the standard DB by applying statistical modeling to the vectorized plurality of medical images.

13. The image processing method according to claim 12, further comprising:
receiving bio-information about the patient to be subjected to the diagnosis as a variable; and
computing the predictive local motion vector by applying the received variable to a function corresponding to the standard DB,
wherein the normalization according to the plurality of regions uses the computed predictive local motion vector.

14. The image processing method according to claim 13,
wherein the established standard DB further comprises local motion vector information corresponding to the plurality of medical images,
wherein the method further comprises:
  searching the local motion vector corresponding to bio-information about the patient to be subjected to the diagnosis from the standard DB; and
  determining the predictive local motion vector based on results of the search, and
wherein the normalization according to the plurality of regions uses the determined predictive local motion vector.

15. The image processing method according to claim 10, further comprising:
  registering a predictive local motion vector generated from the standard DB to a third medical image generated by registration between the first medical image and the second medical image,
  wherein the normalization according to the plurality of regions uses the predictive local motion vector warped to the third medical image by the registration to normalize the local motion vector according to the plurality of regions.

* * * * *